(12) United States Patent
Sesto Yague et al.

(10) Patent No.: US 8,871,729 B2
(45) Date of Patent: Oct. 28, 2014

(54) TREATMENT OF CNS CONDITIONS

(75) Inventors: Angela Sesto Yague, Madrid (ES);
Eduardo Gomez-Acebo Gullon, Madrid (ES); Ma Concepción Jiménez Gomez, Madrid (ES); Ana Isabel Jiménez Antón, Madrid (ES)

(73) Assignee: Sylentis, S.A.U., Madrid (ES)

( * ) Notice: Subject to any disclaimer, the term of this patent is extended or adjusted under 35 U.S.C. 154(b) by 522 days.

(21) Appl. No.: 12/293,230

(22) PCT Filed: Mar. 16, 2007

(86) PCT No.: PCT/GB2007/050128
§ 371 (c)(1),
(2), (4) Date: Dec. 23, 2008

(87) PCT Pub. No.: WO2007/107789
PCT Pub. Date: Sep. 27, 2007

(65) Prior Publication Data
US 2009/0176728 A1    Jul. 9, 2009

(30) Foreign Application Priority Data
Mar. 17, 2006   (GB) .................................. 0605337.5

(51) Int. Cl.
| *A61K 31/70* | (2006.01) |
| *C12N 15/113* | (2010.01) |
| *C12Q 1/68* | (2006.01) |
| *A61K 39/00* | (2006.01) |

(52) U.S. Cl.
CPC .......... *C12N 15/113* (2013.01); *C12N 2320/32* (2013.01); *A61K 2039/543* (2013.01); *C12N 2310/14* (2013.01)
USPC ....... 514/44 A; 536/23.1; 536/24.1; 536/24.5; 435/375; 435/377

(58) Field of Classification Search
None
See application file for complete search history.

(56) References Cited

U.S. PATENT DOCUMENTS

| 6,410,046 | B1* | 6/2002 | Lerner ........................... 424/434 |
| 2004/0192629 | A1* | 9/2004 | Xu et al. ......................... 514/44 |
| 2004/0241854 | A1 | 12/2004 | Davidson |
| 2005/0008617 | A1 | 1/2005 | Chen |
| 2005/0042646 | A1 | 2/2005 | Davidon |
| 2005/0159376 | A1 | 7/2005 | McSwiggen et al. |
| 2005/0222061 | A1 | 10/2005 | Schulte |
| 2005/0265927 | A1 | 12/2005 | Lee |
| 2006/0003989 | A1 | 1/2006 | Quay |
| 2009/0264506 | A1* | 10/2009 | Reinhard et al. ............. 514/44 A |

FOREIGN PATENT DOCUMENTS

| EP | 0616032 | 9/1994 |
| EP | 1385937 | 2/2004 |
| GB | 2406568 | 4/2005 |
| GB | 2415961 | 1/2006 |
| WO | WO 02/086105 | 10/2002 |
| WO | WO 03/002739 | 1/2003 |
| WO | WO 03/070744 | 8/2003 |
| WO | WO 03/087367 | 10/2003 |
| WO | WO 2004/002402 | 1/2004 |
| WO | WO 2004/029212 | 4/2004 |
| WO | WO 2004/058940 | 7/2004 |
| WO | WO 2005/003350 | 1/2005 |
| WO | WO 2005/004794 | 1/2005 |
| WO | WO 2005/014815 | 2/2005 |
| WO | WO 2005/044976 | 5/2005 |
| WO | WO 2005/045037 | 5/2005 |
| WO | WO 2005/102275 | 11/2005 |
| WO | WO 2005/115358 | 12/2005 |
| WO | WO 2005/116212 | 12/2005 |
| WO | WO 2006/041922 | 4/2006 |

OTHER PUBLICATIONS

Dhanda et al., Drug Delivery Technology vol. 5:64-72, 2005.*
Akashi et al., "Suppression of Gene Expression by RNA Interference in Cultured Plant Cells," Antisense Nucleic Acid Drug Dev, 2001, 11(6):359-367.
Banerjee et al., "Control of Developmental Timing by Small Temporal RNAs: a Paradigm for RNA-mediated Regulation of Gene Expression," Bioessays, 2002, 24(2):119-129.
Bitko et al., "Inhibition of Respiratory Viruses by Nasally Administered SiRNA," Nature Medicine, Jan. 2005, 11(1):50-55.
Bosher et al., "RNA Interference: Genetic Wand and Genetic Watchdog." Nat Cell Biol, 2000, 2(2):E31-6.
Caplen et al., "Specific inhibition of Gene Expression by Small Double Stranded RNAs in Invertebrate and Vertebrate Systems," Proc. Natl. Acad. Sci. USA, 2001,98: 9742-9747.
Elbashir et al., "RNA Interference is Mediated by 21- and 22-Nucleotide RNAs," Genes Dev, 2001, 15(2):188-200.
Fire et al., "Potent and Specific Genetic Interference by Double Stranded RNA in a *Caenorhabditis elegans*," Nature, 1998, 391(6669):806-11.
Gil et al., "Induction of Apoptosis by the dsRNA-dependent Protein Kinase (PKR): Mechanism of Action," Apoptosis, 2000, 5(2):107-114.
Graff et al., "Nasal Drug Administration: Potential for Targeted Central Nervous System Delivery," Journal of Pharmaceutical Sciences, Jun. 2005, 94(6):1187-1195.
Grosshans et al., "Micro-RNAs: Small is Plentiful," J Cell Biol, 2002, 156(1):17-21.
Hardy et al., "The Amyloid Hypothesis of Alzheimer's Disease: Progress and Problems on the Road to Therapeutics," Science, 2002, 297(5580):353-356.
Houlden et al., "Corticobasal Degeneration and Progressive Supranuclear Palsy Share a Common Tau Haplotype," Neurology, 2001, 56:1702-1706.
Hutton et al., "Association of Missense and 5'-splice-site mutations in Tau with the Inherited Dementia FTDP-17," Nature, 1998, 393:702-705.

(Continued)

*Primary Examiner* — Sean McGarry
(74) *Attorney, Agent, or Firm* — Margaret B. Brivanlou; Leslie A. Serunian; King & Spalding LLP

(57) ABSTRACT

Methods and compositions for the treatment of pathologic conditions of the central nervous system (CNS) by means of intranasal administration of a composition that modulates, by means of RNA interference, the expression and/or activity of genes involved in above-mentioned conditions.

14 Claims, 12 Drawing Sheets

(56) References Cited

OTHER PUBLICATIONS

Krutzfeldt et al., "Silencing of microRNAs in vivo with 'Antagomirs'," Nature, 2005, 438(7068):685-689.
Lee et al., "Neurodegenerative Tauopathies," Annual Review Neuroscience, 2001, 24:1121-1159.
Lewis et al., "Enhanced Neurofibrillary Degeneration in Transgenic Mice Expressing Mutant Tau and APP," Science, 2001, 293(5534):1487-1491.
Matsuoka Yasuji et al., "Intranasal NAP Administration Reduces Accumulation of Amyloid Peptide and tau Hyperphosphorylation in a Transgenic Mouse Model of Alzheimer's Disease at Early Pathological Stage," Journal of Molecular Neuroscience, 2007, 31(2):165-170.
Miller et al., "Allele-specific Silencing of Dominant Disease Genes," Proceedings of the National Academy of Sciences of USA, Jun. 10, 2003, 100(12):7195-7200.
Miller et al., "Targeting Alzheimer's Disease Genes with RNA Interference: an Efficient Strategy for Silencing Mutant Alleles," Nucleic Acid Res., Jan. 30, 2004, 32(2):661-668.
Mullan et al., "A Pathogenic Mutation for Probable Alzheimer's Disease in the APP Gene at the N-terminus of Beta Amyloid," Nat. Genet., Aug. 1992, 1(5):345-347.
Oddo et al., "Triple-transgenic Model of Alzheimer's Disease with Plaques and Tangles: Intracellular Abeta and Synaptic Dysfunction," Neuron, 2003, 39(3):409-421.
Paddison et al., "Short hairpin RNAs (shRNAs) Induce Sequence-Specific Silencing in Mammalian Cells," Genes Dev, 2002, 16(8):948-958.
Poorkaj et al., "Tau is a candidate Gene for Chromosome 17 Frontotemporal Dementia," Ann. Neurol., Jun. 1998, 43(6):815-825.
Sapru et al., "Silencing of Human alpha-synuclein in vitro and in Rat Brain using Lentiviral-Mediated RNAi" Experimental Neurology, Jan. 7, 2006, 198(2):382-390.
Tatebayashi Yoshitaka et al., "c-jun N-terminal Kinase Hyperphosphorylates R406W tau at the PHF-1 Site During Mitosis," The Faseb Journal: Official Publication of the Federation of American Societies for Experimental Biology, Feb. 14, 2006, 20(6):762-764.
Tuschl et al., "Targeted mRNA Degradation by Double-stranded RNA in vitro," Genes Dev., 1999, 13(24):3191-3197.
Uprichard et al., "The Therapeutic Potential of RNA Interference," Febs Letters, Oct. 31, 2005, 579(26):5996-6007.
Wianny et al., "Specific Interference with Gene Function by Double-Stranded RNA in Early Mouse Development," Nat Cell Biol, 2000, 2(2):70-75.
Williams BR, "Role of the Double-Stranded RNA-activated Protein kinase (PKR) in Cell Regulation," Biochem Soc Trans, 1997, 25(2):509-513.
Xie et al., "Harnessing in vivo siRNA Delivery for Drug Discovery and Therapeutic Development," Drug Discovery Today, Jan. 2006, 11(1-2): 67-73.
Semax nasal drops 1%, IMG RAS (Institute of Molecular Genetics, Russian Academy of Sciences) (Russia), Russian State Register of Medicaments for Semax., pp. 749-750, 2003.
Aravin et al., "Role of Double-Stranded RNA in Eukaryotic Gene Silencing," Mol. Biol. (Mosk.), 36(2), pp. 240-251, Mar.-Apr. 2002, Abstract Only.
Banan et al., "The Ins and Outs of RNAi in Mammalian Cells," Current Pharmaceutical Biotechnology, 5, pp. 441-450, 2004.
Courtney SW. "Multiple Sclerosis—Managing Symptoms. 3$^{rd}$ Edition." *Multiple Sclerosis Society of America*, http://www.msassociation.org/pdfs/manage.pdf pp. 1-110, 2003.
Elabashir et al., "Duplexes of 21-Nucleotide RNAs mediate RNA interference in Cultured Mammalian Cells," Nature, May 24, 2001, 411(6836):494-498.
Elbashir et al., "Functional Anatomy of siRNAs for Mediating Efficient RNAi in *Drosophila melanogaster* Embryo Lysate," EMBO Journal, vol. 20, No. 23, pp. 6877-6888, 2001.
Embry AF. "Multiple Sclerosis—Best Bet Treatment." Online publication on *Direct MS*, http://www.direct-ms.org/bestbet.html, pp. 1-10, retrieved on May 18, 2012.
Hammond et al., "Post-Transcriptional Gene Silencing by Double-Standed RNA," Nature, 2001, 2:110-119.
Mahato et al., "Modulation of Gene Expression by Antisense and Antigene Oligodeoxynucleotides and Small Interfering RNA," Expert Opinion on Drug Delivery, Jan. 2005, 2(1):3-28.
Nagahiro I., et al "Toxicity of cationic liposome-DNA complex in lung isografts." *Transplantation*, 69(9):1802-5, 2000.
Scherer et al., "Approaches for the Sequence-Specific Knockdown of mRNA," Nat. Biotechnology, 2003, 21(12):1457-1465.
Shadrina Mi., et al "Rapid induction of neurotrophin mRNAs in rat glial cell cultures by Semax, an adrenocorticotrophic hormone analog," Neuroscience Letters, 308(2):115-118, 2001.
Steven D. Buckingham "RNA interference: from model organisms towards therapy for neural and neuromuscular disorder," Human Molecular Genetics, 13(2):R275-R288, 2004.
Braasch et al,, "Biodistribution of phosphodiester and phosphorothioate siRNA," Bioorg. & Med. Chem. Lett., 14, 1139-1143, 2004.
Butler et al., "Phosphorothioate oligodeoxynucleotides distribute similarly in class A scavenger receptor knockout and wild-type mice," J. Pharmacol. Exper. Ther., 292, 489-496, 2000.
Hamajima et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., 88(2), 205-10, 1998).
Liu et al., "Radiolabeling small RNA with technetium-99m for visualizing cellular delivery and mouse biodistribution," Nucl. Med. Biol., 34, 399-404, 2007.
Morin et al., "Systemic delivery and quantification of unformulated interfering RNAs in vivo," Curr. Topic. Med. Chem., 9, 1117-1129, 2009.
Stalteri and S. Mather, "Hybridization and cell uptake studies with radiolabelled antisense oligonucleotides," Nucl. Med. Comm., 22, 1171-1179, 2001.
Third Party Observations filed by Marks & Clerk on Oct. 29, 2008.
van de Water et al., "Intravenously administered short interfering RNA accumulates in the kidney and selectively suppresses gene function in renal proximal tubules," Drug Metab. & Disp., 34, 1393-1397, 2006.
Zhang et al., "Small Interfering RNA Targeting Heme Oxygenase-1 Enhances Ischemia-Reperfusion-Induced Lung Apoptoisis," Journal of Biological Chemistry, vol. 279, No. 11, pp. 10677-10684, Mar. 2003.
Sylentis S.A., Communication pursuant to Article 94(3) EPC issued for European Patent Application No. 07733553.7, May 22, 2014, 6 pages.

* cited by examiner

Fig. 7A

Missense/Nonsense

| Accession Number | Codon change | Amino acid change | Codon number | Phenotype |
|---|---|---|---|---|
| CM020737 | CGC-CAC | Arg-His | 5 | Frontotemporal dementia |
| CM022222 | CGC-CTC | Arg-Leu | 5 | Supranuclear palsy, progressive |
| CM003942 | AAG-ACG | Lys-Thr | 257 | Frontotemporal dementia, with parkinsonism |
| CM014799 | gATC-GTC | Ile-Val | 260 | Frontotemporal dementia, with parkinsonism |
| CM030233 | cCTG-GTG | Leu-Val | 266 | Frontotemporal dementia |
| CM981233 | GGC-GTC | Gly-Val | 272 | Frontotemporal dementia, with parkinsonism |
| CM981234 | AATa-AAG | Asn-Lys | 279 | Frontotemporal dementia, with parkinsonism |
| CM014584 | tAAT-CAT | Asn-His | 296 | Frontotemporal dementia, with parkinsonism |
| CM993836 | cCCG-TCG | Pro-Ser | 301 | Frontotemporal dementia/corticobasal degeneration |
| CM981235 | CCG-CTG | Pro-Leu | 301 | Frontotemporal dementia, with parkinsonism |
| CM992927 | AGT-AAT | Ser-Asn | 305 | Frontotemporal dementia |
| CM032951 | CTG-CGG | Leu-Arg | 315 | Frontotemporal dementia |
| CM043764 | AAG-ATG | Lys-Met | 317 | Frontotemporal dementia, with parkinsonism |
| CM020738 | TCC-TTC | Ser-Phe | 320 | Frontotemporal dementia |
| CM042738 | CAG-CGG | Gln-Arg | 336 | Frontotemporal dementia |
| CM981236 | gGTG-ATG | Val-Met | 337 | Frontotemporal dementia, with parkinsonism |
| CM003156 | GAG-GTG | Glu-Val | 342 | Frontotemporal dementia |
| CM034824 | TCG-TTG | Ser-Leu | 352 | Respiratory failure |
| CM013000 | AAA-ATA | Lys-Ile | 369 | Frontotemporal dementia, with parkinsonism |
| CM004888 | cGGG-AGG | Gly-Arg | 389 | Frontotemporal dementia |
| CM994385 | cGGG-CGG | Gly-Arg | 389 | Frontotemporal dementia |
| CM981237 | aCGG-TGG | Arg-Trp | 406 | Frontotemporal dementia, with parkinsonism |
| CM043765 | ACG-ATG | Thr-Met | 427 | Frontotemporal dementia |

Splicing

| Accession Number | IVS | Donor/Acceptor | Location | Substitution | Phenotype |
|---|---|---|---|---|---|
| CS991445 | 9 | ds | +33 | G-A | Frontotemporal dementia |
| CS034626 | 9 | as | -177 | C-T | Frontotemporal dementia. |

Fig. 7B

| | | | | | association with |
|---|---|---|---|---|---|
| CS994525 | 10 | ds | -64 | T-C | Frontotemporal dementia, with parkinsonism |
| CS003183 | 10 | ds | -28 | T-C | Frontotemporal dementia/corticobasal degeneration |
| CS004157 | 10 | ds | -1 | T-C | Supranuclear palsy, progressive |
| CS982264 | 10 | ds | +3 | G-A | Frontotemporal dementia, with parkinsonism |
| CS012211 | 10 | ds | +11 | T-C | Frontotemporal dementia, with parkinsonism |
| CS000864 | 10 | ds | +12 | C-T | Frontotemporal dementia |
| CS982261 | 10 | ds | +13 | A-G | Frontotemporal dementia, with parkinsonism |
| CS982262 | 10 | ds | +14 | C-T | Frontotemporal dementia, with parkinsonism |
| CS982263 | 10 | ds | +16 | C-T | Frontotemporal dementia, with parkinsonism |
| CS033125 | 10 | ds | +19 | C-G | Frontotemporal dementia |
| CS033126 | 10 | ds | +29 | G-A | Frontotemporal dementia |
| CS000463 | 11 | ds | +34 | A-G | Alzheimer disease, increased risk, association |

Regulatory

| Accession Number | Sequence | Phenotype |
|---|---|---|
| CR994768 | CCCGAAGGAGGACACCCACCCCC ACAACGA(G-C)ACAAAGACTCCAACTACAGGAG GTGGAGAA -266 relative to transcription initiation site | Supranuclear palsy, progressive, association with |

Small deletions

| Accession Number | Deletion | Codon | Phenotype |
|---|---|---|---|
| CD991787 | GATAATT^AATaagAAG CTGGATC | 279 | Frontotemporal dementia |
| CD013179 | CTCAAAG^GATaatATC AAACACG | 295 | Frontotemporal dementia, with parkinsonism |

Fig. 8A

| Microtubule associated protein tau 1 (MAPT) | |
|---|---|
| SEQ ID 1 | GTGATGGAAGATCACGCTG |
| SEQ ID 2 | GATCACGCTGGGACGTACG |
| SEQ ID 3 | AGATCAGGGGGGCTACACC |
| SEQ ID 4 | GATCAGGGGGGCTACACCA |
| SEQ ID 5 | GACCAAGAGGGTGACACGG |
| SEQ ID 6 | GAGGGTGACACGGACGCTG |
| SEQ ID 7 | AGAATCCCCTGCAGACC |
| SEQ ID 8 | GAATCTCCCCTGCAGACCC |
| SEQ ID 9 | TCTCCCCTGCAGACCCCCA |
| SEQ ID 10 | CCGGGCTCTGAAACCTCTG |
| SEQ ID 11 | ACCTCTGATGCTAAGAGCA |
| SEQ ID 12 | CCTCTGATGCTAAGAGCAC |
| SEQ ID 13 | GAGCACTCCAACAGCGGAA |
| SEQ ID 14 | CAGCGGAAGATGTGACAGC |
| SEQ ID 15 | GATGTGACAGCACCCTTAG |
| SEQ ID 16 | GCAGGCTGCCGCGCAGCCC |
| SEQ ID 17 | GGAACCACAGCTGAAGAAG |
| SEQ ID 18 | CCACAGCTGAAGAAGCAGG |
| SEQ ID 19 | GAAGCAGGCATTGGAGACA |
| SEQ ID 20 | GCAGGCATTGGAGACACCC |
| SEQ ID 21 | GACGAAGCTGCTGGTCACG |
| SEQ ID 22 | GCTGCTGGTCACGTGACCC |
| SEQ ID 23 | GAGCCTGAAAGTGGTAAGG |
| SEQ ID 24 | AGTGGTAAGGTGGTCCAGG |
| SEQ ID 25 | GTGGTAAGGTGGTCCAGGA |
| SEQ ID 26 | GGTGGTCCAGGAAGGCTTC |
| SEQ ID 27 | GGCTTCCTCCGAGAGCCAG |
| SEQ ID 28 | CCTTCGGGGACAGGACCTG |
| SEQ ID 29 | GCACCAGCTTCTAGGAGAC |
| SEQ ID 30 | GGGGGCAGGGGGCAAAGAG |
| SEQ ID 31 | AGAGAGGCCGGGGAGCAAG |
| SEQ ID 32 | GAGAGGCCGGGGAGCAAGG |
| SEQ ID 33 | GGAGGAGGTGGATGAAGAC |
| SEQ ID 34 | GACCGCGACGTCGATGAGT |
| SEQ ID 35 | GACTCCCCTCCCTCCAAGG |
| SEQ ID 36 | GGCCTCCCCAGCCCAAGAT |
| SEQ ID 37 | GATGGGCGGCCTCCCCAGA |
| SEQ ID 38 | GCCACCAGCATCCCAGGCT |
| SEQ ID 39 | AGTTTCCACAGAGATCCCA |
| SEQ ID 40 | GTTTCCACAGAGATCCCAG |
| SEQ ID 41 | AGGGCAGGATGCCCCCTG |
| SEQ ID 42 | GGGCAGGATGCCCCCTGG |
| SEQ ID 43 | ATCACACCAACGTGCAGA |
| SEQ ID 44 | TCACACCCAACGTGCAGAA |
| SEQ ID 45 | CGTGCAGAAGGAGCAGGCG |
| SEQ ID 46 | GGAGCAGGCGCACTCGGAG |
| SEQ ID 47 | GGGCTGCATTTCCAGGGGC |
| SEQ ID 48 | AAGAGGCTGACCTTCCAGA |
| SEQ ID 49 | AGAGGCTGACCTTCCAGAG |
| SEQ ID 50 | GAGGCTGACCTTCCAGAGC |
| SEQ ID 51 | AAGCAGCCTGCTGCTGCTC |
| SEQ ID 52 | AGCAGCCTGCTGCTGCTCC |
| SEQ ID 53 | GCAGCCTGCTGCTGCTCCG |
| SEQ ID 54 | GCCCGTCAGCCGGGTCCCT |
| SEQ ID 55 | CTCAAAGCTCGCATGGTCA |
| SEQ ID 56 | AGCTCGCATGGTCAGTAAA |
| SEQ ID 57 | GCTCGCATGGTCAGTAAAA |
| SEQ ID 58 | AAGCAAAGACGGGACTGGA |
| SEQ ID 59 | AGCAAAGACGGGACTGGAA |
| SEQ ID 60 | GCAAAGACGGGACTGGAAG |
| SEQ ID 61 | AGACGGGACTGGAAGCGAT |
| SEQ ID 62 | GACGGGACTGGAAGCGATG |
| SEQ ID 63 | GCGATGACAAAAAAGCCAA |
| SEQ ID 64 | AAAAGCCAAGACATCCACA |
| SEQ ID 65 | AAAGCCAAGACATCCACAC |
| SEQ ID 66 | AAGCCAAGACATCCACACG |
| SEQ ID 67 | AGCCAAGACATCCACACGT |
| SEQ ID 68 | GCCAAGACATCCACACGTT |
| SEQ ID 69 | GACATCCACACGTTCCTCT |
| SEQ ID 70 | AACCTTGAAAAATAGGCCT |
| SEQ ID 71 | ACCTTGAAAAATAGGCCTT |
| SEQ ID 72 | CCTTGAAAAATAGGCCTTG |
| SEQ ID 73 | AAATAGGCCTTGCCTTAGC |
| SEQ ID 74 | AATAGGCCTTGCCTTAGCC |
| SEQ ID 75 | ATAGGCCTTGCCTTAGCCC |
| SEQ ID 76 | TAGGCCTTGCCTTAGCCCC |
| SEQ ID 77 | ACACCCCACTCCTGGTAGC |
| SEQ ID 78 | CACCCCACTCCTGGTAGCT |
| SEQ ID 79 | CCCTCCAGCCCTGCTGTGT |
| SEQ ID 80 | ACACGTCTCTTCTGTCACT |
| SEQ ID 81 | CACGTCTCTTCTGTCACTT |
| SEQ ID 82 | CTGGCAGTTCTGGAGCAAA |
| SEQ ID 83 | AGGAGATGAAACTCAAGGG |
| SEQ ID 84 | GGAGATGAAACTCAAGGGG |
| SEQ ID 85 | ACTCAAGGGGGCTGATGGT |
| SEQ ID 86 | CTCAAGGGGGCTGATGGTA |
| SEQ ID 87 | GGGGGCTGATGGTAAAACG |
| SEQ ID 88 | AACGAAGATCGCCACACCG |
| SEQ ID 89 | ACGAAGATCGCCACACCGC |
| SEQ ID 90 | CGAAGATCGCCACACCGCG |
| SEQ ID 91 | GATCGCCACACCGCGGGGA |
| SEQ ID 92 | GGGCCAGGCCAACGCCACC |
| SEQ ID 93 | CGCCACCAGGATTCCAGCA |
| SEQ ID 94 | AAACCCCGCCCGCTCCAAA |
| SEQ ID 95 | AACCCCGCCCGCTCCAAAG |

Fig. 8B

| SEQ ID | Sequence | SEQ ID | Sequence |
|---|---|---|---|
| SEQ ID 96 | ACCCCGCCCGCTCCAAAGA | SEQ ID 129 | ACCAGTTGACCTGAGCAAG |
| SEQ ID 97 | CCCCGCCCGCTCCAAAGAC | SEQ ID 130 | CCAGTTGACCTGAGCAAGG |
| SEQ ID 98 | AGACACCACCCAGCTCTGG | SEQ ID 131 | GGTGACCTCCAAGTGTGGC |
| SEQ ID 99 | GACACCACCCAGCTCTGGT | SEQ ID 132 | GTGTGGCTCATTAGGCAAC |
| SEQ ID 100 | CCTCCAAAATCAGGGGATC | SEQ ID 133 | CATCCATCATAAACCAGGA |
| SEQ ID 101 | AATCAGGGGATCGCAGCGG | SEQ ID 134 | ACCAGGAGGTGGCCAGGTG |
| SEQ ID 102 | ATCAGGGGATCGCAGCGGC | SEQ ID 135 | CCAGGAGGTGGCCAGGTGG |
| SEQ ID 103 | TCAGGGGATCGCAGCGGCT | SEQ ID 136 | GTAAAATCTGAGAAGCTTG |
| SEQ ID 104 | CCCCACCCACCCGGGAGCC | SEQ ID 137 | AATCTGAGAAGCTTGACTT |
| SEQ ID 105 | GAAGGTGGCAGTGGTCCGT | SEQ ID 138 | ATCTGAGAAGCTTGACTTC |
| SEQ ID 106 | GGTGGCAGTGGTCCGTACT | SEQ ID 139 | TCTGAGAAGCTTGACTTCA |
| SEQ ID 107 | GTCGCCGTCTTCCGCCAAG | SEQ ID 140 | GCTTGACTTCAAGGACAGA |
| SEQ ID 108 | GAGCCGCCTGCAGACAGCC | SEQ ID 141 | GGACAGAGTCCAGTCGAAG |
| SEQ ID 109 | GAATGTCAAGTCCAAGATC | SEQ ID 142 | GATTGGGTCCCTGGACAAT |
| SEQ ID 110 | TGTCAAGTCCAAGATCGGC | SEQ ID 143 | TATCACCCACGTCCCTGGC |
| SEQ ID 111 | GTCCAAGATCGGCTCCACT | SEQ ID 144 | ATAAAAAGATTGAAACCCA |
| SEQ ID 112 | GATCGGCTCCACTGAGAAC | SEQ ID 145 | TAAAAAGATTGAAACCCAC |
| SEQ ID 113 | CCTGAAGCACCAGCCGGGA | SEQ ID 146 | AAAGATTGAAACCCACAAG |
| SEQ ID 114 | GCACCAGCCGGGAGGCGGG | SEQ ID 147 | AAGATTGAAACCCACAAGC |
| SEQ ID 115 | GGTGCAGATAATTAATAAG | SEQ ID 148 | AGATTGAAACCCACAAGCT |
| SEQ ID 116 | TTAATAAGAAGCTGGATCT | SEQ ID 149 | GATTGAAACCCACAAGCTG |
| SEQ ID 117 | TAAGAAGCTGGATCTTAGC | SEQ ID 150 | ACCCACAAGCTGACCTTCC |
| SEQ ID 118 | GAAGCTGGATCTTAGCAAC | SEQ ID 151 | CCCACAAGCTGACCTTCCG |
| SEQ ID 119 | GCTGGATCTTAGCAACGTC | SEQ ID 152 | GCTGACCTTCCGCGAGAAC |
| SEQ ID 120 | CGTCCAGTCCAAGTGTGGC | SEQ ID 153 | CGCCAAAGCCAAGACAGAC |
| SEQ ID 121 | GTGTGGCTCAAAGGATAAT | SEQ ID 154 | AGCCAAGACAGACCACGGG |
| SEQ ID 122 | AGGATAATATCAAACACGT | SEQ ID 155 | GCCAAGACAGACCACGGGG |
| SEQ ID 123 | GGATAATATCAAACACGTC | SEQ ID 156 | GACAGACCACGGGGCGGAG |
| SEQ ID 124 | TATCAAACACGTCCCGGGA | SEQ ID 157 | GTCGCCAGTGGTGTCTGGG |
| SEQ ID 125 | ACACGTCCCGGGAGGCGGC | SEQ ID 158 | TGTCTCCTCCACCGGCAGC |
| SEQ ID 126 | CACGTCCCGGGAGGCGGCA | SEQ ID 159 | TATTAAACACGTCCTGGGA |
| SEQ ID 127 | ATAGTCTACAAACCAGTTG | SEQ ID 160 | ACGTCTCCATGGCATCTCA |
| SEQ ID 128 | TAGTCTACAAACCAGTTGA | | |

Fig. 8C

| Microtubule associated protein tau 1 (MAPT) | | |
|---|---|---|
| | 5' | GUGAUGGAAGAUCACGCUG 3' |
| SEQ ID 161 | | ||||||||||||||||||| |
| | 3' | CACUACCUUCUAGUGCGAC 5' |
| | 5' | GAUCACGCUGGGACGUACG 3' |
| SEQ ID 162 | | ||||||||||||||||||| |
| | 3' | CUAGUGCGACCCUGCAUGC 5' |
| | 5' | AGAUCAGGGGGGCUACACC 3' |
| SEQ ID 163 | | ||||||||||||||||||| |
| | 3' | UCUAGUCCCCCGAUGUGG 5' |
| | 5' | GAUCAGGGGGGCUACACC 3' |
| SEQ ID 164 | | ||||||||||||||||||| |
| | 3' | CUAGUCCCCCGAUGUGGUA 5' |
| | 5' | GACCAAGAGGGUGACACGG 3' |
| SEQ ID 165 | | ||||||||||||||||||| |
| | 3' | CUGGUUCUCCCACUGUGCC 5' |
| | 5' | GAGGGUGACACGGACGCUG 3' |
| SEQ ID 166 | | ||||||||||||||||||| |
| | 3' | CUCCCACUGUGCCUGCGAC 5' |
| | 5' | AGAAUCUCCCCUCCAGACC 3' |
| SEQ ID 167 | | ||||||||||||||||||| |
| | 3' | UCUUAGAGGGGACGUCUGG 5' |
| | 5' | GAAUCUCCCCUGCAGACCC 3' |
| SEQ ID 168 | | ||||||||||||||||||| |
| | 3' | CUUAGAGGGGACGUCUGGG 5' |
| | 5' | UCUCCCCUGCAGACCCCCA 3' |
| SEQ ID 169 | | ||||||||||||||||||| |
| | 3' | AGAGGGGACGUCUGGGGGU 5' |
| | 5' | CCCGCCCUCUGAAACCUCUG 3' |
| SEQ ID 170 | | ||||||||||||||||||| |
| | 3' | GGCCCGAGACUUUGGAGAC 5' |
| | 5' | ACCUCUGAUGCUAAGAGCA 3' |
| SEQ ID 171 | | ||||||||||||||||||| |
| | 3' | UGGAGACUACGAUUCUCGU 5' |
| | 5' | CCUCUGAUGCUAAGAGCAC 3' |
| SEQ ID 172 | | ||||||||||||||||||| |
| | 3' | GGAGACUACGAUUCUCGUG 5' |
| | 5' | GAGCACUCCAACAGCGGAA 3' |
| SEQ ID 173 | | ||||||||||||||||||| |
| | 3' | CUCGUGAGGUUGUCGCCUU 5' |
| | 5' | CAGCGGAAGAUGUGACAGC 3' |
| SEQ ID 174 | | ||||||||||||||||||| |
| | 3' | GUCGCCUUCUACACUGUCG 5' |
| | 5' | GAUGUGACAGCACCCUUAG 3' |
| SEQ ID 175 | | ||||||||||||||||||| |
| | 3' | CUACACUGUCGUGGGAAUC 5' |
| | 5' | GCAGGCUGCCGCGCAGCCC 3' |
| SEQ ID 176 | | ||||||||||||||||||| |
| | 3' | CGUCCGACGGCGCGUCGGG 5' |
| | 5' | GGAACCACAGCUGAAGAAG 3' |
| SEQ ID 177 | | ||||||||||||||||||| |
| | 3' | CCUUGGUGUCGACUUCUUC 5' |
| | 5' | CCACAGCUGAAGAAGCAGC 3' |
| SEQ ID 178 | | ||||||||||||||||||| |
| | 3' | GGUGUCGACUUCUUCGUCC 5' |
| | 5' | GAAGCAGGCAUUGGAGACA 3' |
| SEQ ID 179 | | ||||||||||||||||||| |
| | 3' | CUUCGUCCGUAACCUCUGU 5' |
| | 5' | GCAGGCAUUGGAGACACCC 3' |
| SEQ ID 180 | | ||||||||||||||||||| |
| | 3' | CGUCCGUAACCUCUGUGGG 5' |
| | 5' | GACGAAGCUGCUGGUCACG 3' |
| SEQ ID 181 | | ||||||||||||||||||| |
| | 3' | CUGCUUCGACGACCAGUGC 5' |
| | 5' | GCUGCUGGUCACCUCACCC 3' |
| SEQ ID 182 | | ||||||||||||||||||| |
| | 3' | CGACGACCAGUGCACUGGG 5' |
| | 5' | GAGCCUGAAAGUGGUAAGG 3' |
| SEQ ID 183 | | ||||||||||||||||||| |
| | 3' | CUCGGACUUUCACCAUUCC 5' |
| | 5' | AGUGGUAAGGUGGUCCAGG 3' |
| SEQ ID 184 | | ||||||||||||||||||| |
| | 3' | UCACCAUUCCACCAGGUCC 5' |
| | 5' | GUGGUAAGGUGGUCCAGGA 3' |
| SEQ ID 185 | | ||||||||||||||||||| |
| | 3' | CACCAUUCCACCAGGUCCU 5' |
| | 5' | GGUGGUCCAGGAAGGCUUC 3' |
| SEQ ID 186 | | ||||||||||||||||||| |
| | 3' | CCACCAGGUCCUUCCGAAG 5' |
| | 5' | GGCUUCCUCCGAGAGCCAG 3' |
| SEQ ID 187 | | ||||||||||||||||||| |
| | 3' | CCGAAGGAGGCUCUCGGUC 5' |
| | 5' | CCUUCGGGACAGGACCUG 3' |
| SEQ ID 188 | | ||||||||||||||||||| |
| | 3' | GGAAGCCCUGUCCUGGAC 5' |
| | 5' | GCACCAGCUUCUAGGAGAC 3' |
| SEQ ID 189 | | ||||||||||||||||||| |
| | 3' | CGUGGUCGAAGAUCCUCUG 5' |
| | 5' | GGGGGCAGGGGGCAAACAG 3' |
| SEQ ID 190 | | ||||||||||||||||||| |
| | 3' | CCCCCGUCCCCGUUUCUC 5' |
| | 5' | AGAGAGGCCGGGGAGCAAG 3' |
| SEQ ID 191 | | ||||||||||||||||||| |
| | 3' | UCUCUCCGGCCCCUCGUUC 5' |
| | 5' | GAGAGGCCGGGGAGCAAGG 3' |
| SEQ ID 192 | | ||||||||||||||||||| |
| | 3' | CUCUCCGGCCCCUCGUUCC 5' |
| | 5' | GGAGGAGGUGGAUGAAGAC 3' |
| SEQ ID 193 | | ||||||||||||||||||| |
| | 3' | CCUCCUCCACCUACUUCUG 5' |
| | 5' | GACCGCGACGUCGAUGAGU 3' |
| SEQ ID 194 | | ||||||||||||||||||| |
| | 3' | CUGGCGCUGCAGCUACUCA 5' |
| | 5' | GACUCCCCUCCCUCCAAGG 3' |
| SEQ ID 195 | | ||||||||||||||||||| |
| | 3' | CUGAGGGGAGGGAGGUUCC 5' |
| | 5' | GGCCUCCCCAGCCCAAGAU 3' |
| SEQ ID 196 | | ||||||||||||||||||| |
| | 3' | CCGGAGGGGUCGGGUUCUA 5' |
| | 5' | GAUGGGCGGCCUCCCCAGA 3' |
| SEQ ID 197 | | ||||||||||||||||||| |
| | 3' | CUACCCGCCGGAGGGGUCU 5' |
| | 5' | GCCACCAGCAUCCCAGGCU 3' |
| SEQ ID 198 | | ||||||||||||||||||| |
| | 3' | CGGUGGUCGUAGGGUCCGA 5' |
| | 5' | AGUUCCACAGAGAUCCCA 3' |
| SEQ ID 199 | | ||||||||||||||||||| |
| | 3' | UCAAAGGUGUCUCUAGGGU 5' |
| | 5' | GUUUCCACAGAGAUCCCAG 3' |
| SEQ ID 200 | | ||||||||||||||||||| |
| | 3' | CAAAGGUGUCUCUAGGGUC 5' |
| | 5' | AGGGCAGGAUGCCCCCCUG 3' |
| SEQ ID 201 | | ||||||||||||||||||| |
| | 3' | UCCCGUCCUACGGGGGAC 5' |
| | 5' | GGGCAGGAUGCCCCCCUGG 3' |
| SEQ ID 202 | | ||||||||||||||||||| |
| | 3' | CCCGUCCUACGGGGGACC 5' |
| | 5' | AUCAUACCCAACGUGCAGA 3' |
| SEQ ID 203 | | ||||||||||||||||||| |
| | 3' | UAGUGUGGGUUGCACGUCU 5' |
| | 5' | UCACACCCAACGUGCAGAA 3' |
| SEQ ID 204 | | ||||||||||||||||||| |
| | 3' | AGUGUGGGUUGCACGUCUU 5' |
| | 5' | CCUGCAGAAGGAGCAGGCG 3' |
| SEQ ID 205 | | ||||||||||||||||||| |
| | 3' | GCACGUCUUCCUCGUCCGC 5' |

Fig. 8D

| | | |
|---|---|---|
| SEQ ID 206 | 5' GGAGCAGGCGCACUCGGAG 3'<br>　　　\|\|\|\|\|\|\|\|　\|\|\|\|　\|\|\|\|<br>3' CCUCGUCCGCGUGAGCCUC 5' | |
| SEQ ID 207 | 5' GGGCUGCAUUUCCAGGGGC 3'<br>　　　\|\|\|\|\|\|\|\|　\|\|\|\|　\|\|\|\|<br>3' CCCGACGUAAAGGUCCCCG 5' | |
| SEQ ID 208 | 5' AAGAGGCUGACCUUCCAGA 3'<br>　　　\|\|\|\|\|\|\|\|　\|\|\|\|　\|\|\|\|<br>3' UUCUCCGACUGGAAGGUCU 5' | |
| SEQ ID 209 | 5' AGAGGCUGACCUUCCAGAG 3'<br>　　　\|\|\|\|\|\|\|\|　\|\|\|\|　\|\|\|\|<br>3' UCUCCGACUGGAAGGUCUC 5' | |
| SEQ ID 210 | 5' GAGGCUGACCUUCCAGAGC 3'<br>　　　\|\|\|\|\|\|\|\|　\|\|\|\|　\|\|\|\|<br>3' CUCCGACUGGAAGGUCUCG 5' | |
| SEQ ID 211 | 5' AAGCAGCCUGCUGCUGCUC 3'<br>　　　\|\|\|\|\|\|\|\|\|　\|\|\|\|　\|\|\|\|<br>3' UUCGUCGGACGACGACGAG 5' | |
| SEQ ID 212 | 5' AGCAGCCUGCUGCUGCUCC 3'<br>　　　\|\|\|\|\|\|\|\|\|　\|\|\|\|　\|\|\|\|<br>3' UCGUCGGACGACGACGAGG 5' | |
| SEQ ID 213 | 5' GCAGCCUGCUGCUCUCCG 3'<br>　　　\|\|\|\|\|\|\|\|\|　\|\|\|\|　\|\|\|\|<br>3' CGUCGGACGACGACGAGGC 5' | |
| SEQ ID 214 | 5' GCCCGUCAGCCGGGUCCCU 3'<br>　　　\|\|\|\|\|\|\|\|\|　\|\|\|\|　\|\|\|\|<br>3' CGGGCAGUCGGCCCAGGGA 5' | |
| SEQ ID 215 | 5' CUCAAAGCUCGCAUGGUCA 3'<br>　　　\|\|\|\|\|\|\|\|\|　\|\|\|\|　\|\|\|\|<br>3' GAGUUUCGAGCGUACCAGU 5' | |
| SEQ ID 216 | 5' AGCUCGCAUGGUCAGUAAA 3'<br>　　　\|\|\|\|\|\|\|\|\|　\|\|\|\|\|　\|\|\|\|<br>3' UCGAGCGUACCAGUCAUUU 5' | |
| SEQ ID 217 | 5' GCUCGCAUGGUCAGUAAAA 3'<br>　　　\|\|\|\|\|\|\|\|\|　\|\|\|\|\|\|\|\|\|\|<br>3' CGAGCGUACCAGUCAUUUU 5' | |
| SEQ ID 218 | 5' AAGCAAAGACGGGACUGGA 3'<br>　　　\|\|\|\|\|\|\|\|\|　\|\|\|\|\|　\|\|\|\|<br>3' UUCGUUUCUGCCCUGACCU 5' | |
| SEQ ID 219 | 5' AGCAAAGACGGGACUGGAA 3'<br>　　　\|\|\|\|\|\|\|\|\|\|\|\|\|\|　\|\|\|\|<br>3' UCGUUUCUGCCCUGACCUU 5' | |
| SEQ ID 220 | 5' GCAAAGACGGGACUGGAAG 3'<br>　　　\|\|\|\|\|\|\|\|\|\|\|\|\|\|　\|\|\|\|<br>3' CGUUUCUGCCCUGACCUUC 5' | |
| SEQ ID 221 | 5' AGACGGGACUGGAAGCGAU 3'<br>　　　\|\|\|\|\|\|\|\|\|\|\|\|\|\|　\|\|\|\|<br>3' UCUGCCCUGACCUUCGCUA 5' | |
| SEQ ID 222 | 5' GACGGGACUGGAAGCGAUG 3'<br>　　　\|\|\|\|\|\|\|\|\|\|\|\|\|\|　\|\|\|\|<br>3' CUGCCCUGACCUUCGCUAC 5' | |
| SEQ ID 223 | 5' GCGAUGACAAAAAAGCCAA 3'<br>　　　\|\|\|\|\|\|\|\|\|\|\|\|\|\|\|\|\|\|\|<br>3' CGCUACUGUUUUUUCGGUU 5' | |
| SEQ ID 224 | 5' AAAAGCCAAGACAUCCACA 3'<br>　　　\|\|\|\|\|\|\|\|\|\|\|\|\|\|\|\|\|\|\|<br>3' UUUUCGGUUCUGUAGGUGU 5' | |
| SEQ ID 225 | 5' AAAGCCAAGACAUCCACAC 3'<br>　　　\|\|\|\|\|\|\|\|\|\|\|\|\|\|\|\|\|\|\|<br>3' UUUCGGUUCUGUAGGUGUG 5' | |
| SEQ ID 226 | 5' AAGCCAAGACAUCCACACG 3'<br>　　　\|\|\|\|\|\|\|\|\|\|\|\|\|\|\|\|\|\|\|<br>3' UUCGGUUCUGUAGGUGUGC 5' | |
| SEQ ID 227 | 5' AGCCAAGACAUCCACACGU 3'<br>　　　\|\|\|\|\|\|\|\|\|\|\|\|\|\|\|\|\|\|\|<br>3' UCGGUUCUGUAGGUGUGCA 5' | |
| SEQ ID 228 | 5' GCCAAGACAUCCACACGUU 3'<br>　　　\|\|\|\|\|\|\|\|\|\|\|\|\|\|\|\|\|\|\|<br>3' CGGUUCUGUAGGUGUGCAA 5' | |
| SEQ ID 229 | 5' GACAUCCACACGUUCCUCU 3'<br>　　　\|\|\|\|\|\|\|\|\|\|\|\|\|\|\|\|\|\|\|<br>  | |
| SEQ ID 230 | 3' CUGUAGGUGUGCAAGGACA 5'<br>　　　\|\|\|\|\|\|\|\|\|\|\|\|\|\|\|\|\|\|\|<br>5' AACCUUGAAAAAUAGGCCU 3'<br>3' UUGGAACUCUUUAUCCGGA 5' | |
| SEQ ID 231 | 5' ACCUUGAAAAAUAGGCCUU 3'<br>　　　\|\|\|\|\|\|\|\|\|\|\|\|\|\|\|\|\|\|\|<br>3' UGGAACUUUUUAUCCGGAA 5' | |
| SEQ ID 232 | 5' CCUUGAAAAAUAGGCCUUG 3'<br>　　　\|\|\|\|\|\|\|\|\|\|\|\|\|\|\|\|\|\|\|<br>3' GGAACUUUUUAUCCGGAAC 5' | |
| SEQ ID 233 | 5' AAAUACGCCUUGCCUUAGC 3'<br>　　　\|\|\|\|\|\|\|\|\|\|\|\|\|\|\|\|\|\|\|<br>3' UUUAUCCGGAACGGAAUCG 5' | |
| SEQ ID 234 | 5' AAUAGGCCUUGCCUUAGCC 3'<br>　　　\|\|\|\|\|\|\|\|\|\|\|\|\|\|\|\|\|\|\|<br>3' UUAUCCGGAACGGAAUCGG 5' | |
| SEQ ID 235 | 5' AUAGGCCUUGCCUUAGCCC 3'<br>　　　\|\|\|\|\|\|\|\|\|\|\|\|\|\|\|\|\|\|\|<br>3' UAUCCGGAACGGAAUCGGG 5' | |
| SEQ ID 236 | 5' UAGGCCUUGCCUUAGCCCC 3'<br>　　　\|\|\|\|\|\|\|\|\|\|\|\|\|\|\|\|\|\|\|<br>3' AUCCGGAACGGAAUCGGGG 5' | |
| SEQ ID 237 | 5' ACACCCCACUCCUGGUAGC 3'<br>　　　\|\|\|\|\|\|\|\|\|\|\|\|\|\|\|\|\|\|\|<br>3' UGUGGGGUGAGGACCAUCG 5' | |
| SEQ ID 238 | 5' CACCCCACUCCUGGUAGCU 3'<br>　　　\|\|\|\|\|\|\|\|\|\|\|\|\|\|\|\|\|\|\|<br>3' GUGGGGUGAGGACCAUCGA 5' | |
| SEQ ID 239 | 5' CCCUCCAGCCCUGCUGUGU 3'<br>　　　\|\|\|\|\|\|\|\|\|\|\|\|\|\|\|\|\|\|\|<br>3' GGGAGGUCGGGACGACACA 5' | |
| SEQ ID 240 | 5' ACACGUCUCUUCUGUCACU 3'<br>　　　\|\|\|\|\|\|\|\|\|\|\|\|\|\|\|\|\|\|\|<br>3' UGUGCAGAGAAGACAGUGA 5' | |
| SEQ ID 241 | 5' CACGUCUCUUCUGUCACUU 3'<br>　　　\|\|\|\|\|\|\|\|\|\|\|\|\|\|\|\|\|\|\|<br>3' GUGCAGAGAAGACAGUGAA 5' | |
| SEQ ID 242 | 5' CUGGCAGUUCUGGAGCAAA 3'<br>　　　\|\|\|\|\|\|\|\|\|\|\|\|\|\|\|\|\|\|\|<br>3' GACCGUCAAGACCUCGUUU 5' | |
| SEQ ID 243 | 5' AGGAGAUGAAACUCAAGGG 3'<br>　　　\|\|\|\|\|\|\|\|\|\|\|\|\|\|\|\|\|\|\|<br>3' UCCUCUACUUUGAGUUCCC 5' | |
| SEQ ID 244 | 5' GGAGAUGAAACUCAAGGGG 3'<br>　　　\|\|\|\|\|\|\|\|\|\|\|\|\|\|\|\|\|\|\|<br>3' CCUCUACUUUGAGUUCCCC 5' | |
| SEQ ID 245 | 5' ACUCAAGGGGGCUGAUGGU 3'<br>　　　\|\|\|\|\|\|\|\|\|\|\|\|\|\|\|\|\|\|\|<br>3' UGAGUUCCCCCGACUACCA 5' | |
| SEQ ID 246 | 5' CUCAAGGGGGCUGAUGGUA 3'<br>　　　\|\|\|\|\|\|\|\|\|\|\|\|\|\|\|\|\|\|\|<br>3' GAGUUCCCCCGACUACCAU 5' | |
| SEQ ID 247 | 5' GGGGGCUGAUGGUAAAACG 3'<br>　　　\|\|\|\|\|\|\|\|\|\|\|\|\|\|\|\|\|\|\|<br>3' CCCCCGACUACCAUUUUGC 5' | |
| SEQ ID 248 | 5' AACGAAGAUCGCCACACCG 3'<br>　　　\|\|\|\|\|\|\|\|\|\|\|\|\|\|\|\|\|\|\|<br>3' UUGCUUCUAGCGGUGUGGC 5' | |
| SEQ ID 249 | 5' ACGAAGAUCGCCACACCGC 3'<br>　　　\|\|\|\|\|\|\|\|\|\|\|\|\|\|\|\|\|\|\|<br>3' UGCUUCUAGCGGUGUGGCG 5' | |
| SEQ ID 250 | 5' CGAAGAUCGCCACACCGCG 3'<br>　　　\|\|\|\|\|\|\|\|\|\|\|\|\|\|\|\|\|\|\|<br>3' GCUUCUAGCGGUGUGGCGC 5' | |
| SEQ ID 251 | 5' GAUCGCCACACCGCGGGGA 3'<br>　　　\|\|\|\|\|\|\|\|\|\|\|\|\|\|\|\|\|\|\|<br>3' CUAGCGGUGUGGCGCCCCU 5' | |
| SEQ ID 252 | 5' GGGCCAGGCCAACGCCACC 3'<br>　　　\|\|\|\|\|\|\|\|\|\|\|\|\|\|\|\|\|\|\|<br>3' CCCGGUCCGGUUGCGGUGG 5' | |

Fig. 8E

SEQ ID 253
5' CGCCACCAGGAUUCCAGCA 3'
   |||||||||||||| |||
3' GCGGUGGUCCUAAGGUCGU 5'

SEQ ID 254
5' AAACCCCGCCCGCUCCAAA 3'
   |||||||||||||| |||
3' UUUGGGGCGGGCGAGGUUU 5'

SEQ ID 255
5' AACCCCGCCCGCUCCAAAG 3'
   |||||||||||||| |||
3' UUGGGGCGGGCGAGGUUUC 5'

SEQ ID 256
5' ACCCCGCCCGCUCCAAAGA 3'
   || |||||||||||| |||
3' UGGGGCGGGCGAGGUUUCU 5'

SEQ ID 257
5' CCCCCGCCCGCUCCAAAGAC 3'
   || |||||||||||| |||
3' GGGGCGGGCGAGGUUUCUG 5'

SEQ ID 258
5' AGACACCACCCAGCUCUGG 3'
   || |||||||||||| |||
3' UCUGUGGUGGGUCGAGACC 5'

SEQ ID 259
5' GACACCACCCAGCUCUGGU 3'
   || ||||||||||| |||
3' CUGUGGUGGGUCGAGACCA 5'

SEQ ID 260
5' CCUCCAAAAUCAGGGGAUC 3'
   || |||||||||||| |||
3' GGAGGUUUUAGUCCCCUAG 5'

SEQ ID 261
5' AAUCAGGGGAUCGCAGCGG 3'
   || |||||||||||| |||
3' UUAGUCCCCUAGCGUCGCC 5'

SEQ ID 262
5' AUCAGGGGAUCGCAGCGGC 3'
   | ||| ||||||||||| ||
3' UAGUCCCUAGCGUCGCCG 5'

SEQ ID 263
5' UCAGGGGAUCGCAGCGGCU 3'
   || ||||||||||| |||
3' AGUCCCCUAGCGUCGCCGA 5'

SEQ ID 264
5' CCCCACCCACCCGGGAGCC 3'
   || ||||||||||| |||
3' GGGGUGGGUGGGCCCUCGG 5'

SEQ ID 265
5' GAAGGUGGCAGUGGUCCGU 3'
   || ||||||||||||| |||
3' CUUCCACCGUCACCAGGCA 5'

SEQ ID 266
5' GGUGGCAGUGGUCCGUACU 3'
   ||| |||||||||||| |||
3' CCACCGUCACCAGGCAUGA 5'

SEQ ID 267
5' GUCGCCGUCUUCCGCCAAG 3'
   |||||||||||||||
3' CAGCGGCAGAAGGCGGUUC 5'

SEQ ID 268
5' GAGCCGCCUGCAGACAGCC 3'
   |||||||||||||||
3' CUCGGCGGACGUCUGUCGG 5'

SEQ ID 269
5' GAAUGUCAAGUCCAAGAUC 3'
   |||||||||||||||
3' CUUACAGUUCAGGUUCUAG 5'

SEQ ID 270
5' UGUCAAGUCCAAGAUCGGC 3'
   |||||||||||||||
3' ACAGUUCAGGUUCUAGCCG 5'

SEQ ID 271
5' GUCCAAGAUCGGCUCCACU 3'
   ||||||||||||||
3' CAGGUUCUAGCCGAGGUGA 5'

SEQ ID 272
5' GAUCGGCUCCACUGAGAAC 3'
   |||||||||||| ||
3' CUAGCCGAGGUGACUCUUG 5'

SEQ ID 273
5' CCUGAAGCACCAGCCGGGA 3'
   ||||||||||||| ||
3' GGACUUCGUGGUCGGCCCU 5'

SEQ ID 274
5' GCACCAGCCGGGAGGCGGG 3'
   |||||| ||||||||||
3' CGUGGUCGGCCCUCCGCCC 5'

SEQ ID 275
5' GGUGCAGAUAAUUAAUAAG 3'
   ||||| ||||||||||
3' CCACGUCUAUUAAUUAUUC 5'

SEQ ID 276
5' UUAAUAACAAGCUGGAUCU 3'
   |||||| |||||||||||

SEQ ID 277
3' AAUUAUUCUUCGACCUAGA 5'
5' UAAGAAGCUGGAUCUUAGC 3'
   |||||||||||||||
3' AUUCUUCGACCUAGAAUCG 5'

SEQ ID 278
5' GAAGCUGGAUCUUAGCAAC 3'
   |||||||||||||||
3' CUUCGACCUAGAAUCGUUG 5'

SEQ ID 279
5' GCUGGAUCUUAGCAACGUC 3'
   |||||||||||||||
3' CGACCUAGAAUCGUUGCAG 5'

SEQ ID 280
5' CGUCCAGUCCAAGUGUGGC 3'
   |||||||||||||||
3' GCAGGUCAGGUUCACACCG 5'

SEQ ID 281
5' GUGUGGCUCAAAGGAUAAU 3'
   |||||||||||||||
3' CACACCGAGUUUCCUAUUA 5'

SEQ ID 282
5' AGGAUAAUAUCAAACACGU 3'
   |||||||||||||||
3' UCCUAUUAUAGUUUGUGCA 5'

SEQ ID 283
5' GGAUAAUAUCAAACACGUC 3'
   |||||||||||||||
3' CCUAUUAUAGUUUGUGCAG 5'

SEQ ID 284
5' UAUCAAACACGUCCCGGGA 3'
   |||||||||||||||
3' AUAGUUUGUGCAGGGCCCU 5'

SEQ ID 285
5' ACACGUCCCGGGAGGCGGC 3'
   |||||||||||||||
3' UGUGCAGGGCCCUCCGCCG 5'

SEQ ID 286
5' CACCUCCCGGGAGGCGGCA 3'
   |||||||||||||||
3' GUGCAGGGCCCUCCGCCGU 5'

SEQ ID 287
5' AUAGUCUACAAACCAGUUG 3'
   |||||||||||||||
3' UAUCAGAUGUUUGGUCAAC 5'

SEQ ID 288
5' UAGUCUACAAACCAGUUGA 3'
   |||||||||||||||
3' AUCAGAUGUUUGGUCAACU 5'

SEQ ID 289
5' ACCAGUUGACCUCAGCAAG 3'
   |||||||||||||||
3' UGGUCAACUGGACUCGUUC 5'

SEQ ID 290
5' CCAGUUGACCUGAGCAAGG 3'
   |||||||||||||||
3' GGUCAACUGGACUCGUUCC 5'

SEQ ID 291
5' GGUGACCUCCAAGUGUGGC 3'
   |||||||||||||||
3' CCACUGGAGGUUCACACCG 5'

SEQ ID 292
5' GUGUGGCUCAUUAGGCAAC 3'
   |||||||||||||||
3' CACACCGAGUAAUCCGUUG 5'

SEQ ID 293
5' CAUCCAUCAUAAACCAGGA 3'
   |||||||||||||||
3' GUAGGUAGUAUUUGGUCCU 5'

SEQ ID 294
5' ACCAGGAGGUGGCCAGGUG 3'
   |||||||||||||||
3' UGGUCCUCCACCGGUCCAC 5'

SEQ ID 295
5' CCAGGAGGUGGCCAGGUGG 3'
   |||||||||||||||
3' GGUCCUCCACCGGUCCACC 5'

SEQ ID 296
5' GUAAAAUCUGAGAAGCUUG 3'
   |||||||||||||||
3' CAUUUUAGACUCUUCGAAC 5'

SEQ ID 297
5' AAUCUGAGAAGCUUGACUU 3'
   |||||||||||||||
3' UUAGACUCUUCGAACUGAA 5'

SEQ ID 298
5' AUCUGAGAAGCUUGACUUC 3'
   |||||||||||||||
3' UAGACUCUUCGAACUGAAG 5'

SEQ ID 299
5' UCUGAGAAGCUUGACUUCA 3'
   |||||||||||||||
3' AGACUCUUCGAACUGAAGU 5'

Fig. 8F

```
                 5'  GCUUGACUUCAAGGACAGA  3'                          5'  ACCCACAAGCUGACCUUCC  3'
                     |||  |||||||||||||||                                 |||||||||||||||||||
SEQ ID 300       3'  CGAACUGAAGUUCCUGUCU  5'       SEQ ID 310        3'  UGGGUGUUCGACUGGAAGG  5'
                 5'  GGACAGAGUCCAGUCGAAG  3'                          5'  CCCACAACCUGACCUUCCG  3'
                     |||  ||||||||||||||                                 ||||| |||||||||||||
SEQ ID 301       3'  CCUGUCUCAGGUCAGCUUC  5'       SEQ ID 311        3'  GGGUGUUCGACUGGAAGGC  5'
                 5'  GAUUGGGUCCCUGGACAAU  3'                          5'  CCUCACCUUCCCCCACAAC  3'
                     |||  |||||||||||||||                                 |||||||||||||||||||
SEQ ID 302       3'  CUAACCCAGGGACCUGUUA  5'       SEQ ID 312        3'  CGACUGGAAGGCGCUCUUG  5'
                                                                      5'  CGCCAAAGCCAAGACAGAC  3'
                                                                         |||||||||||||||||||
                 5'  UAUCACCCACGUCCCUGGC  3'       SEQ ID 313        3'  GCGGUUCGGUUCUGUCUG  5'
                     |||:|||||||||||||||                              5'  AGCCAAGACAGACCACGGG  3'
SEQ ID 303       3'  AUAGUGGGUGCAGGGACCG  5'                             |||||||||  |||||||||
                 5'  AUAAAAAGAUUGAAACCCA  3'       SEQ ID 314        3'  UCGGUUCUGUCUGGUGCCC  5'
                     |||||||||||||||||||                              5'  GCCAAGACAGACCACGGGG  3'
SEQ ID 304       3'  UAUUUUUCUAACUUUGGGU  5'                             ||||||||| |||||||||
                 5'  UAAAAAGAUUGAAACCCAC  3'       SEQ ID 315        3'  CGGUUCUGUCUGGUGCCCC  5'
                     |||||||||||||||||  ||                             5'  GACAGACCACGGGGCGGAG  3'
SEQ ID 305       3'  AUUUUUCUAACUUUGGGUG  5'                             |||||||  ||||||||||
                 5'  AAAGAUUGAAACCCACAAG  3'       SEQ ID 316        3'  CUGUCUGGUGCCCCGCCUC  5'
                     ||||||||||||||||| ||                              5'  GUCGCCAGUGGUGUCUGGG  3'
SEQ ID 306       3'  UUUCUAACUUUGGGUGUUC  5'                             ||||||| |||||||||:|
                 5'  AAGAUUGAAACCCACAAGC  3'       SEQ ID 317        3'  CAGCGGUCACCACAGACCC  5'
                     |||||||||||||||| ||                              5'  UGUCUCCUCCACCGGCAGC  3'
SEQ ID 307       3'  UUCUAACUUUGGGUGUUCG  5'                             |||||||| |||||||| |
                 5'  AGAUUGAAACCCACAAGCU  3'       SEQ ID 318        3'  ACAGAGCAGGUGGCCGUCG  5'
                     |||||||||||||||||:||
SEQ ID 308       3'  UCUAACUUUGGGUGUUCGA  5'                         5'-UAUUAAACACGUCCUGGGA- 3'
                 5'  GAUUGAAACCCACAAGCUG  3'                            |||||||||||||||||||
                     |||||||||||||||||||              SEQ ID 319     3'-AUAAUUUGUGCAGGACCCU- 5'
SEQ ID 309       3'  CUAACUUUGGGUGUUCGAC  5'
                                                                      5'-ACGUCUCCAUGGCAUCUCA- 3'
                                                                         |||||||||||||||||||
                                                     SEQ ID 320      3'-UGCAGAGGUACCGUAGAGU- 5'
```

TREATMENT OF CNS CONDITIONS

SEQUENCE LISTING

The instant application contains a Sequence listing which has been submitted electronically in ASCII format and is hereby incorporated by reference in its entirety. The ASCII copy of the Sequence Listing, created on Jul. 21, 2014, is referred to as 14262-105004_SL.txt and is 61,910 bytes in size.

FIELD OF THE INVENTION

The present invention relates to methods and compositions for the treatment of pathologic conditions of the central nervous system (CNS) by means of intranasal administration of a composition that modulates, by means of RNA interference, the expression and/or activity of genes involved in above-mentioned conditions. The compositions of the invention comprise short interfering nucleic acid molecules (siNA) and related compounds including, but not limited to, small-interfering RNAs (siRNA). In preferred embodiments, intranasally delivered siNA molecules targeting tau, huntingtin, acetyleholinesterase, as well as mutated alleles of these or other genes of the CNS, are useful in the preparation of a medicament for the treatment of diseases of the CNS such as dementia, Alzheimer's, Huntington's and/or Parkinson's diseases, as well as congenital diseases associated with mutations of genes of the CNS amongst others.

BACKGROUND OF THE INVENTION

RNAi as a Tool to Modulate Gene Expression

RNA interference refers to the process of sequence-specific post-transcriptional gene silencing mediated by double-stranded RNA (dsRNA). After the discovery of the phenomenon in plants in the early 1990s, Andy Fire and Craig Mello demonstrated that dsRNA specifically and selectively inhibited gene expression in an extremely efficient manner in *Caenorhabditis elegans* (Fire et al., 1998). The sequence of the first strand (sense RNA) coincided with that of the corresponding region of the target messenger RNA (mRNA). The second strand (antisense RNA) was complementary to the mRNA. The resulting dsRNA turned out to be several orders of magnitude more efficient than the corresponding single-stranded RNA molecules (in particular, antisense RNA).

The process of RNAi begins when the enzyme DICER encounters dsRNA and chops it into pieces called small-interfering RNAs or siRNA. This protein belongs to the RNase III nuclease family. A complex of proteins gathers up these RNA remains and uses their code as a guide to search out and destroy any RNAs in the cell with a matching sequence, such as target mRNA (see Bosher & Labouesse, 2000; and Akashi et al., 2001).

In attempting to apply RNAi for gene knockdown, it was recognized that mammalian cells have developed various protective mechanisms against viral infections that could impede the use of this approach. Indeed, the presence of extremely low levels of viral dsRNA triggers an interferon response, resulting in a global non-specific suppression of translation, which in turn triggers apoptosis (Williams, 1997, Gil & Esteban, 2000).

In 2000, dsRNA was reported to specifically inhibit three genes in the mouse oocyte and early embryo. Translational arrest, and thus a PKR response, was not observed as the embryos continued to develop (Wianny & Zernicka-Goetz, 2000). Research at Ribopharma AG (Kulmbach, Germany) demonstrated the functionality of RNAi in mammalian cells, using short (20-24 base pairs) dsRNAs to switch off genes in human cells without initiating the acute-phase response. Similar experiments carried out by other research groups confirmed these results (Elbashir et al., 2001; Caplen et al., 2001). Tested in a variety of normal and cancer human and mouse cell lines, it was determined that short hairpin RNAs (shRNAs) can silence genes as efficiently as their siRNA counterparts (Paddison et al., 2002). Recently, another group of small RNAs (21-25 base pairs) was shown to mediate downregulation of gene expression. These RNAs, small temporally regulated RNAs (stRNAs), regulate timing of gene expression during development in *Caenorhabditis elegans* (for review see Banerjee & Slack, 2002 and Grosshans & Slack, 2002).

Scientists have used RNAi in several systems, including *Caenorhabditis elegans, Drosophila*, trypanosomes, and other invertebrates. Several groups have recently presented the specific suppression of protein biosynthesis in different mammalian cell lines (specifically in HeLa cells) demonstrating that RNAi is a broadly applicable method for gene silencing in vitro. Based on these results, RNAi has rapidly become a well recognized tool for validating (identifying and assigning) gene functions. RNAi employing short dsRNA oligonucleotides will yield an understanding of the function of genes being only partially sequenced.

Recently, Krutzfeldt and colleagues have shown that a class of specially engineered compounds called 'antagomirs' can effectively silence the action of microRNAs (miRNAs), non-coding pieces of RNA that regulate gene expression (Knitzfeldt et al., 2005).

Intranasal Delivery of siNA Products

Aerosol delivery of nucleic acids to the lungs using viral vectors, polymers, surfactants, or excipients, has been described for the treatment of lung diseases. Suitable nucleic acids for intranasal delivery have been suggested as including dsDNA, dsRNA, ssDNA, ssRNA, short interfering RNA, micro-RNA, and antisense RNA (see US2005/0265927, and WO2005/115358).

Preferred delivery agents for RNAi-inducing agents into the lung include cationic polymers, modified cationic polymers, lipids, and surfactants suitable for introduction (see US20050008617).

Delivery into the CNS

Intranasal delivery for the treatment of CNS diseases has only been attained with acetylcholinesterase inhibitors such as galantamine and various salts and derivatives of galantamine (see for example US2006003989, WO2004/002402, WO2005/102275), while treatment of neurodegenerative disorders by means of discharging small interfering RNA into the CNS has previously been obtained by surgically implanting a catheter (see for example WO2005/116212). WO02/086105 describes methods for delivery of oligonucleotides to the CNS via neural pathways originating in the nasal cavity. The use of antisense oligonucleotides is discussed, but no reference to RNA interference is made. Further, there is no disclosure in this publication of physiological activity of the delivered oligonucleotides. Intravenously administered siNA have further been demonstrated to cross the blood-retina barrier and modulate expression of genes in the eye (WO03/087367, US2005/0222061). Modulation of the expression of certain genes involved in Alzheimer's disease, such as beta-secretase (BACE), amyloid precursor protein (APP), PIN-1, presenilin 1 (PS-1) and/or presenilin 2 (PS-2), as well as that of genes involved in Huntington's disease, such as huntingtin or ataxin-1, has already been attained with siNA both in cell culture as well as in vivo by means of strategies including intrathecal and intracerebroventricular administration, implantation of catheters and pumps, by chemical or osmotic opening of the blood-brain barrier, or by direct injection or perfusion into the brain arterial system (i.e.: into the striatum, cortex)—see for example WO2005/003350, US2005/042646, and GB2415961).

Tau Targeting by Means of RNAi

Tau has a central role in inherited and acquired forms of age-related dementia, including Alzheimer's disease (AD) (Hardy & Selkoe, 2002; Lee et al., 2001; Mullan et al., 1992; Poorkaj et al., 1998; Hutton et al., 1998). AD is characterized by two major pathological hallmarks: senile plaques, which contain beta-amyloid (AP) derived from cleavage of amyloid precursor protein (APP); and neurofibrillary tangles, which contain filamentous tau protein. Rare inherited forms of AD have revealed an essential role for AP production in the pathogenesis of all forms of AD, both sporadic and inherited (Hardy & Selkoe, 2002). Mutations in the three genes known to cause familial AD—the genes encoding APP, presenilin 1 and presenilin 2—act dominantly to enhance the production of neurotoxic beta-amyloid (Hardy & Selkoe, 2002).

Tau, the major component of neurofibrillary tangles, likewise plays a significant role in AD pathogenesis (Lee et al., 2001). Mutations in tau cause a similar dominantly inherited neurodegenerative disease, frontotemporal dementia with parkinsonism linked to chromosome 17 (FTDP-17). In FTDP-17, tau mutations either alter the tau protein sequence or lead to aberrant splicing (Lee et al., 2001; Lewis et al., 2001; Oddo et al., 2003). Abnormalities of tau expression also contribute to several other important neurodegenerative disorders, including progressive supranuclear palsy and corticalbasal ganglionic degeneration (Houlden et al., 2001). Thus, efforts to reduce tau expression, either generally or in an allele-specific manner, may prove to be therapeutically useful in FTDP-17, AD or other tau-related diseases.

Allele-specific silencing of tau mutations and/or associated single-nucleotide polymorphisms (SNP) by means of RNAi has already been achieved in cell cultures (Miller et al. 2003, 2004). Further, siRNA of interest were successfully delivered onto a mouse model by means of injection into the tail vein (US2004/0241854).

The preceding is a discussion of relevant art pertaining to RNAi as well as of delivery approaches into the CNS. The discussion is provided only for understanding of the invention that follows, and is not an admission that any of the work described is prior art to the claimed invention. There is a need not met by the art for convenient methods whereby siNA molecules may be delivered to the CNS, and whereby such delivery results in RNA interference activity. We have developed techniques for modulating gene expression in vivo to treat CNS diseases by means of targeting siRNA molecules to the CNS by intranasal administration.

SUMMARY OF THE INVENTION

The present invention provides methods and compositions for the treatment of pathologies of the central nervous system (CNS) by means of intranasal administration of compounds which cause RNA interference.

The compositions of the invention comprise short interfering nucleic acid molecules (siNA) and related compounds including, but not limited to, small interfering RNA (siRNA), double-stranded RNA (dsRNA), short hairpin RNA (shRNA), micro-RNA (miRNA), antagomirs, and molecules capable of mediating RNA interference.

The methods of the invention comprise the administration to a patient in the need thereof of an effective amount of one or more siNA of the invention for the treatment of a CNS pathological condition. In preferred embodiments, the methods of the invention comprise intranasal administration of the therapeutic siNA. In particular, the compositions of the invention can be used in the preparation of a medicament for the treatment of CNS pathologies including dementia, Alzheimer's, Huntington's and/or Parkinson's diseases, as well as congenital diseases associated with mutations of genes of the CNS amongst others. Pathologies and diseases which may be treated according to the methods of the invention preferably include those affecting the hippocampus, the cortex, and/or the striatum.

In one embodiment, the present invention relates to siNA or similar chemically synthesized entities, that are directed at interfering with the mRNA expression of tau, huntingtin or acetyleholinesterase genes, as well as of mutated alleles of these or other genes of the CNS that ultimately modulate the amount of protein produced. In preferred embodiments, compositions of the present invention are intranasally administered for specifically targeting the abnormal version of the gene of interest within the CNS.

BRIEF DESCRIPTION OF THE FIGURES

The invention will be described by way of example only with reference to the following figures.

FIGS. 7A and 7B. List of MAPT mutations and gene sequence accession numbers.

FIGS. 8A-8F. Sequence listing of regions of MAPT targeted by siNA of the invention (FIGS. 8A-8B), and of siNA duplexes targeting these regions (FIGS. 8C-8F).

DETAILED DESCRIPTION OF THE INVENTION

Figure 1:
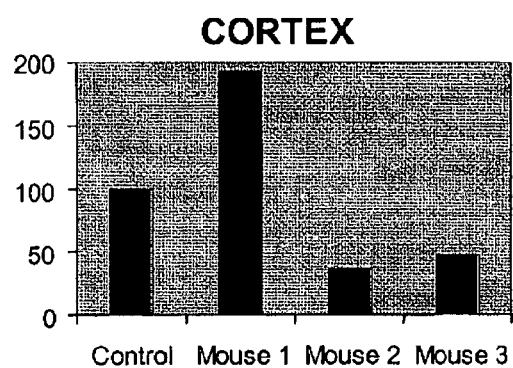
FIG. 1: GFP expression levels after intranasal administration to mice of 0.9% NaCl (Control), 1 nmol/ul siRNA-GFP (Mouse 1), 2 nmol/ul siRNA-GFP (Mouse 2), and 2 nmol/ul siRNA-GFP+TransIT-TKO (Mouse 3). Analysis of cortex, hippocampus, striatum and bulb of the CNS were carried out.
Figure 1:
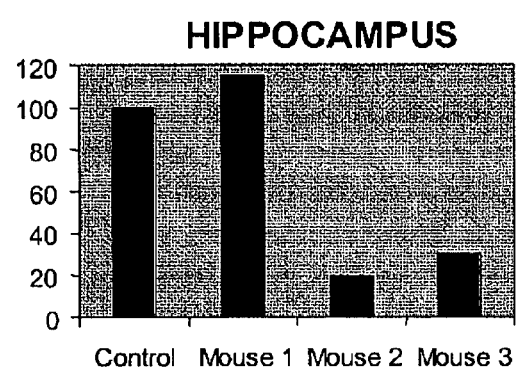
Figure 1:
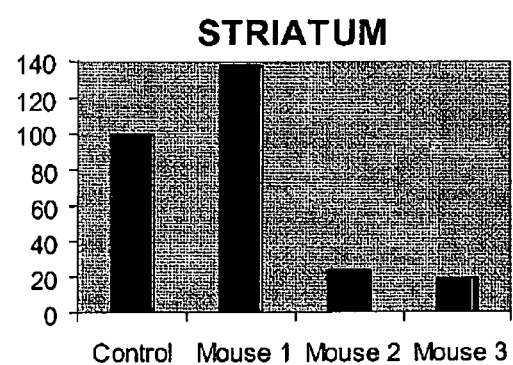
Figure 1:
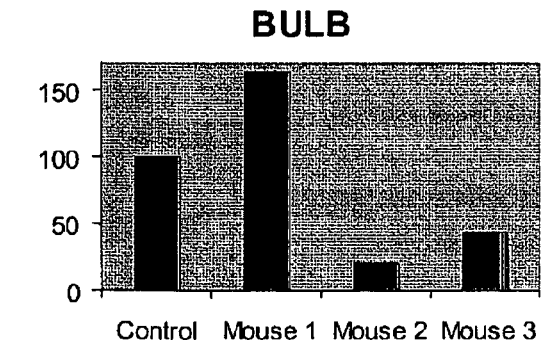

The present invention relates to methods and compositions for the treatment of CNS pathologies by means of intranasal administration of compounds which cause RNAi. The compositions of the invention comprise short interfering nucleic acid molecules (siNA) that modulate the expression of target genes associated with abnormal conditions of the CNS.

The methods of the invention comprise the administration to a patient in need thereof of an effective amount of one or more siNA of the invention.

Design of siRNA

A gene is "targeted" by siNA according to the invention when, for example, the siNA selectively decrease or inhibit the expression of the gene or of an allele of the gene involved in a pathological condition. Alternatively, siNA target a gene when the siNA hybridize under stringent conditions to the gene transcript. siNA can be tested either in vitro or in vivo for the ability to target a gene.

In 1999, Tuschl et al. deciphered the silencing effect of siRNAs showing that their efficiency is a function of the length of the duplex, the length of the 3'-end overhangs, and the sequence in these overhangs.

Selecting the right homologous region within the target gene is of great relevance for accurate silencing. A short fragment of the target gene sequence (e.g., 19-40 nucleotides in length) is chosen as the sequence of the siNA of the invention. Alternatively, the variable region of the allele of interest is selected as target of the siNA compounds. In one embodiment, the siNA is siRNA. In such embodiments, the short fragment of target gene sequence is a fragment of the target gene mRNA. In preferred embodiments, the criteria for choosing a sequence fragment from the target gene mRNA to be a candidate siRNA molecule include: 1) a sequence from the target gene mRNA that is at least 50-100 nucleotides from the 5' or 3' end of the native mRNA molecule; 2) a sequence from the target gene mRNA that has a G/C content of between 30% and 70%, most preferably around 50%; 3) a sequence from the target gene mRNA that does not contain repetitive sequences (e.g., AAA, CCC, GGG, TTT, AAAA, CCCC, GGGG, TTTT); 4) a sequence from the target gene mRNA that is accessible in the mRNA; and 5) a sequence from the target gene mRNA that is unique to the target gene. The sequence fragment from the target gene mRNA may meet one or more of the above-mentioned identified criteria. In preferred embodiments, the siRNA has a G/C content below 60% and/or lacks repetitive sequences.

Practically, the gene of interest is introduced as a nucleotide sequence in a prediction program that takes into account all the variables described above for the design of optimal oligonucleotides. This program scans any mRNA nucleotide sequence for regions susceptible to be targeted by siRNA. The output of this analysis is a score of possible siRNA oligonucleotides. The highest scores are used to design double stranded RNA oligonucleotides (typically 21 bp long, although other lengths are also possible) that are typically made by chemical synthesis. Several chemical modifications that are well known in the art, aimed at increasing stability or availability of the dsRNA oligonucleotides, may also be made.

Candidate oligonucleotides can further be filtered for interspecies sequence conservation in order to facilitate the transition from animal to human clinical studies.

In addition to siNA which is perfectly complementary to the target region, degenerate siNA sequences may be used to target homologous regions. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology. As such, one advantage of using siNAs of the invention is that a single siNA can be designed to include nucleic acid sequence that is complementary to the nucleotide sequence that is conserved between homologous genes. In this approach, a single siNA can be used to inhibit expression of more than one gene instead of using more than one siNA molecule to target different genes.

Sequence identity may be calculated by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, or 99% sequence identity between the siNA and the portion of the target gene is preferred. Alternatively, the complementarity between the siNA and native RNA molecule may be defined functionally by hybridisation as well as functionally by its ability to decrease or inhibit the expression of a target gene. The ability of a siNA to affect gene expression can be determined empirically either in vivo or in vitro.

Preferred siNA molecules of the invention are double stranded. In one embodiment, double stranded siNA molecules comprise blunt ends. In another embodiment, double stranded siNA molecules comprise overhanging nucleotides (e.g., 1-5 nucleotide overhangs, preferably 2 nucleotide overhangs). In a specific embodiment, the overhanging nucleotides are 3' overhangs. In another specific embodiment, the overhanging nucleotides are 5' overhangs. Any type of nucleotide can be a part of the overhang. In one embodiment, the overhanging nucleotide or nucleotides are ribonucleic acids. In another embodiment, the overhanging nucleotide or nucleotides are deoxyribonucleic acids. In a preferred embodiment, the overhanging nucleotide or nucleotides are thymidine nucleotides. In another embodiment, the overhanging nucleotide or nucleotides are modified or non-classical nucleotides. The overhanging nucleotide or nucleotides may have non-classical internucleotide bonds (e.g., other than phosphodiester bond).

Synthesis of siNA Duplexes siNA can be synthesized by any method known in the art. RNAs are preferably chemically synthesized using appropriately protected ribonucleoside phosphoramidites and a conventional DNA/RNA synthesizer. Additionally, siRNA can be obtained from commercial RNA oligo synthesis suppliers, including, but not limited to, Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany) Ambion (USA) and Invitrogen (Scotland). Alternatively, siNA molecules of the invention can be expressed in cells by transfecting the cells with vectors containing the reverse complement siNA sequence under the control of a promoter. Once expressed, the siNA can be isolated from the cell using techniques well known in the art.

An annealing step is necessary when working with single-stranded RNA molecules. To anneal the RNAs, 30 µl of each RNA oligo 50 µM solution are to be combined in 100 mM potassium acetate, 30 mM HEPES-KOH pH 7.4, 2 mM magnesium acetate. The solution is then incubated for 1 minute at 90° C., centrifuged for 15 seconds, and incubated for 1 hour at 37° C.

In embodiments where the siRNA is a short hairpin RNA (shRNA), the two strands of the siRNA molecule may be connected by a linker region (e.g., a nucleotide linker or a non-nucleotide linker).

Chemical Modification of siNA.

The siNAs of the invention may contain one or more modified nucleotides and/or non-phosphodiester linkages. Chemical modifications well known in the art are capable of increasing stability, availability, and/or cell uptake of the siNA. The skilled person will be aware of other types of chemical modification which may be incorporated into RNA molecules (see International Publications WO03/070744 and WO2005/045037 for an overview of types of modifications).

In one embodiment, modifications can be used to provide improved resistance to degradation or improved uptake. Examples of such modifications include phosphorothioate internucleotide linkages, 2'-O-methyl ribonucleotides (especially on the sense strand of a double stranded siRNA), 2'-deoxy-fluoro ribonucleotides, 2'-deoxy ribonucleotides, "universal base" nucleotides, 5-C-methyl nucleotides, and inverted deoxyabasic residue incorporation (see generally GB2406568).

In another embodiment, modifications can be used to enhance the stability of the siRNA or to increase targeting efficiency. Modifications include chemical cross linking between the two complementary strands of an siRNA, chemical modification of a 3' or 5' terminus of a strand of an siRNA, sugar modifications, nucleobase modifications and/or backbone modifications, 2'-fluoro modified ribonucleotides and 2'-deoxy ribonucleotides (see generally International Publication WO2004/029212).

In another embodiment, modifications can be used to increase or decrease affinity for the complementary nucleotides in the target mRNA and/or in the complementary siNA strand (see generally International Publication WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine.

In another embodiment, when the siNA is a double-stranded siRNA, the 3'-terminal nucleotide overhanging nucleotides are replaced by deoxyribonucleotides (see generally Elbashir et al., 2001).

In one embodiment, the invention features a double-stranded short interfering nucleic acid (siNA) molecule that down-regulates expression of a target gene, preferably a gene expressed in the CNS, more preferably a MAPT gene, wherein the siNA molecule is assembled from two separate oligonucleotide fragments wherein one fragment comprises the sense region and the second fragment comprises the antisense region of the siNA molecule. In another embodiment about 19 nucleotides of each fragment of the siNA molecule are base-paired to the complementary nucleotides of the other fragment of the siNA molecule and wherein at least two 3' terminal nucleotides of each fragment of the siNA molecule are not base-paired to the nucleotides of the other fragment of the siNA molecule (that is, the siNA molecule includes overhangs of at least 2 nucleotides on each strand). In one embodiment, each of the two 3' terminal nucleotides of each fragment of the siNA molecule is a 2'-deoxy-pyrimidine nucleotide, such as a 2'-deoxy-thymidine. In another embodiment, all 21 nucleotides of each fragment of the siNA molecule are base-paired to the complementary nucleotides of the other fragment of the siNA molecule. In another embodiment, about 19 nucleotides of the antisense region are base-paired to the nucleotide sequence or a portion thereof of the RNA encoded by the target gene. In another embodiment, about 21 nucleotides of the antisense region are base-paired to the nucleotide sequence or a portion thereof of the RNA encoded by the target gene. In any of the above embodiments, the 5'-end of the fragment comprising said antisense region can optionally include a phosphate group.

In one embodiment, the invention features a siNA molecule, wherein either or both of the sense or antisense strand comprises one or more, for example, about 1, 2, 3, 4, 5, 6, 7, 8, 9, 10, or more, preferably from 1 to 5, phosphorothioate internucleotide linkages, and/or one or more (e.g., about 1, 2, 3, 4, 5, 6, 7, 8, 9, 10 or more), preferably from 1 to 5, 2'-deoxy, 2'-O-methyl, 2'-deoxy-2'-fluoro, and/or about one or more (e.g., about 1, 2, 3, 4, 5, 6, 7, 8, 9, 10 or more), preferably from 1 to 5, universal base modified nucleotides, and optionally a terminal cap molecule at the 3'-end, the 5'-end, or both of the 3'- and 5'-ends of either or both of the sense or antisense strand. In another embodiment, one or more, for example about 1, 2, 3, 4, 5, 6, 7, 8, 9, 10, or more, preferably from 1 to 5, pyrimidine nucleotides of the sense and/or antisense siNA strand are chemically-modified with 2'-deoxy, 2'-O-methyl and/or 2'-deoxy-2'-fluoro nucleotides, optionally with one or more, for example about 1, 2, 3, 4, 5, 6, 7, 8, 9, 10, or more, preferably from 1 to 5, phosphorothioate internucleotide linkages and/or a terminal cap molecule at the 3'-end, the 5'-end, or both of the 3'- and 5'-ends, being present in the same or different strand.

In one embodiment, the invention features a chemically-modified short interfering nucleic acid (siNA) molecule having about 1 to about 5 or more (specifically about 1, 2, 3, 4, 5 or more) phosphorothioate internucleotide linkages in each strand of the siNA molecule.

In another embodiment, the invention features a siNA molecule comprising 2'-5' internucleotide linkages. The 2'-5' internucleotide linkage(s) can be at the 3'-end, the 5'-end, or both of the 3'- and 5'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In one embodiment, a siNA molecule of the invention comprises one or more (e.g., about 1, 2, 3, 4, 5, 6, 7, 8, 9, 10, or more) locked nucleic acid (LNA) nucleotides, for example, at the 5'-end, the 3'-end, both of the 5' and 3'-ends, or any combination thereof of the siNA molecule.

In another embodiment, a siNA molecule of the invention comprises one or more (e.g., about 1, 2, 3, 4, 5, 6, 7, 8, 9, 10, or more) acyclic nucleotides, for example, at the 5'-end, the 3'-end, both of the 5' and 3'-ends, or any combination thereof, of the siNA molecule.

In one embodiment, the invention features a chemically-modified short interfering nucleic acid (siNA) molecule of the invention, wherein any (e.g., one or more or all) pyrimidine nucleotides present in either or both the sense or antisense region are 2'-deoxy-2'-fluoro pyrimidine nucleotides, and wherein any (e.g., one or more or all) purine nucleotides present in either or both the sense or the antisense region are 2'-deoxy purine nucleotides. Optionally, any nucleotides comprising a 3'-terminal nucleotide overhang that are present in said sense or antisense region are 2'-deoxy nucleotides.

In one embodiment, the invention features a chemically-modified short interfering nucleic acid (siNA) molecule of the invention, wherein any (e.g., one or more or all) pyrimidine nucleotides present in either or both the sense or antisense region are 2'-deoxy-2'-fluoro pyrimidine nucleotides, and wherein any (e.g., one or more or all) purine nucleotides present in either or both the sense or antisense region are 2'-O-methyl purine nucleotides. Optionally, any nucleotides comprising a 3'-terminal nucleotide overhang that are present in said sense or antisense region are 2'-deoxy nucleotides.

In one embodiment, the invention features a chemically synthesized double stranded RNA molecule that directs cleavage of a target RNA, preferably an RNA expressed in the CNS, more preferably a MAPT RNA, via RNA interference, wherein each strand of said RNA molecule is about 21 to about 23 nucleotides in length; one strand of the RNA molecule comprises nucleotide sequence having sufficient complementarity to the target RNA for the RNA molecule to direct cleavage of the target RNA via RNA interference; and wherein at least one strand of the RNA molecule comprises one or more chemically modified nucleotides described herein, such as deoxynucleotides, 2'-O-methyl nucleotides, 2'-deoxy-2'-fluoro nucleotides, 2'-O-methoxyethyl nucleotides etc.

In one embodiment, the invention features a medicament comprising a siNA molecule of the invention.

In one embodiment, the invention features an active ingredient comprising a siNA molecule of the invention.

In one embodiment, the invention features the use of a double-stranded short interfering nucleic acid (siNA) molecule to down-regulate expression of a target gene, preferably a gene expressed in the CNS, more preferably a MAPT gene, wherein the siNA molecule comprises one or more chemical modifications and each strand of the double-stranded siNA is about 18 to about 28 or more (e.g., about 18, 19, 20, 21, 22, 23, 24, 25, 26, 27, or 28 or more) nucleotides long.

In one embodiment, the invention features a double-stranded short interfering nucleic acid (siNA) molecule that inhibits expression of a target gene, preferably a gene expressed in the CNS, more preferably a MAPT gene, wherein one of the strands of the double-stranded siNA molecule is an antisense strand which comprises nucleotide sequence that is complementary to nucleotide sequence of target RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. Preferably the target RNA or portion thereof encodes a protein or portion thereof. Optionally, the 5' end of the antisense strand includes a phosphate group. The nucleotide sequence or a portion thereof of the antisense strand may be complementary to a nucleotide sequence of the untranslated region or a portion thereof of the target RNA.

In one embodiment, each strand of the siNA molecule comprises about 18 to about 29 or more (e.g., about 18, 19, 20, 21, 22, 23, 24, 25, 26, 27, 28, or 29 or more) nucleotides, wherein each strand comprises at least about 18 nucleotides that are complementary to the nucleotides of the other strand. In one embodiment, the siNA molecule is assembled from two oligonucleotide fragments, wherein one fragment comprises the nucleotide sequence of the antisense strand of the siNA molecule and a second fragment comprises nucleotide sequence of the sense region of the siNA molecule. In one embodiment, the sense strand is connected to the antisense strand via a linker molecule, such as a polynucleotide linker or a non-nucleotide linker. In a further embodiment, the pyrimidine nucleotides present in the sense strand are 2'-deoxy-2'fluoro pyrimidine nucleotides and the purine nucleotides present in the sense region are 2'-deoxy purine nucleotides. In another embodiment, the pyrimidine nucleotides present in the sense strand are 2'-deoxy-2'fluoro pyrimidine nucleotides and the purine nucleotides present in the sense region are 2'-O-methyl purine nucleotides. In still another embodiment, the pyrimidine nucleotides present in the antisense strand are 2'-deoxy-2'-fluoro pyrimidine nucleotides and any purine nucleotides present in the antisense strand are 2'-deoxy purine nucleotides. In another embodiment, the antisense strand comprises one or more 2'-deoxy-2'-fluoro pyrimidine nucleotides and one or more 2'-O-methyl purine nucleotides. In another embodiment, the pyrimidine nucleotides present in the antisense strand are 2'-deoxy-2'-fluoro pyrimidine nucleotides and any purine nucleotides present in the antisense strand are 2'-O-methyl purine nucleotides. In a further embodiment the sense strand comprises a 3'-end and a 5'-end, wherein a terminal cap moiety (e.g., an inverted deoxy abasic moiety or inverted deoxy nucleotide moiety such as inverted thymidine) is present at the 5'-end, the 3'-end, or both of the 5' and 3' ends of the sense strand. In another embodiment, the antisense strand comprises a phosphorothioate internucleotide linkage at the 3' end of the antisense strand. In another embodiment, the antisense strand comprises a glyceryl modification at the 3' end. In another embodiment, the 5'-end of the antisense strand optionally includes a phosphate group.

In any of the above-described embodiments of a double-stranded short interfering nucleic acid (siNA) molecule that inhibits expression of a target gene, preferably a gene expressed in the CNS, more preferably a MAPT gene, wherein a majority of the pyrimidine nucleotides present in the double-stranded siNA molecule comprises a sugar modification, each of the two strands of the siNA molecule can comprise about 21 nucleotides. In one embodiment, about 21 nucleotides of each strand of the siNA molecule are base-paired to the complementary nucleotides of the other strand of the siNA molecule. In another embodiment, about 19 nucleotides of each strand of the siNA molecule are base-paired to the complementary nucleotides of the other strand of the siNA molecule, wherein at least two 3' terminal nucleotides of each strand of the siNA molecule are not base-paired to the nucleotides of the other strand of the siNA molecule. In another embodiment, each of the two 3' terminal nucleotides of each fragment of the siNA molecule is a 2'-deoxy-pyrimidine, such as 2'-deoxy-thymidine. In one embodiment, each strand of the siNA molecule is base-paired to the complementary nucleotides of the other strand of the siNA molecule. In one embodiment, about 19 nucleotides of the antisense strand are base-paired to the nucleotide sequence of the target RNA or a portion thereof. In one embodiment, about 21 nucleotides of the antisense strand are base-paired to the nucleotide sequence of the target RNA or a portion thereof.

In one embodiment, the invention features a composition comprising a siNA molecule of the invention in a pharmaceutically acceptable carrier or diluent.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

In any of the embodiments of siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

In other embodiments siNA molecules have blunt ends.

In one embodiment, the invention encompasses siNA molecules that are 40 nucleotides or less and comprise a nucleotide sequence of any of SEQ ID NOS:1-160 of FIGS. 8A and 8B. In a specific embodiment, the siNA is 21-30 nucleotides long and comprises any one of SEQ ID NOS:161-320 of FIGS. 8C-8F.

In one embodiment, the invention features a method of modulating the expression of a target gene, preferably a gene expressed in the CNS, more preferably a MAPT gene in a subject or organism comprising: (a) synthesizing a siNA molecule of the invention, which can be chemically-modified, wherein one of the siNA strands comprises a sequence complementary to RNA of the target gene; and (b) introducing the siNA molecule into the subject or organism under conditions suitable to modulate the expression of the target gene in the subject or organism. The level of target protein or RNA can be determined using various methods well-known in the art.

In another embodiment, the invention features a method of modulating the expression of more than one target gene, preferably genes expressed in the CNS, more preferably including at least one MAPT gene in a subject or organism comprising: (a) synthesizing siNA molecules of the invention, which can be chemically-modified, wherein one of the siNA strands comprises a sequence complementary to RNA of the target genes; and (b) introducing the siNA molecules into the subject or organism under conditions suitable to modulate the expression of the target genes in the subject or organism. The level of target protein or RNA can be determined as is known in the art.

In one embodiment, the invention features a method for modulating the expression of a target gene, preferably a gene expressed in the CNS, more preferably a MAPT gene within a cell comprising: (a) synthesizing a siNA molecule of the invention, which can be chemically-modified, wherein the siNA comprises a single stranded sequence having complementarity to RNA of the target gene; and (b) introducing the siNA molecule into a cell under conditions suitable to modulate the expression of the target gene in the cell.

In another embodiment, the invention features a method for modulating the expression of more than one target gene, preferably genes expressed in the CNS, more preferably including at least one MAPT gene within a cell comprising: (a) synthesizing siNA molecules of the invention, which can be chemically-modified, wherein the siNA comprises a single stranded sequence having complementarity to RNA of the target gene; and (b) contacting the cell in vitro or in vivo with the siNA molecule under conditions suitable to modulate the expression of the target genes in the cell.

In Vitro Testing of siRNA Duplexes.

To check the specificity of the siRNA interference, preliminary testing can be carried out in cell cultures expressing target genes.

Basically, the cells are incubated with the corresponding siRNA duplexes, followed by analysis of gene expression levels. For linking siRNA knockdown to specific phenotypes in cultured cells, it is necessary to demonstrate the decrease of the targeted protein or at least to demonstrate the reduction of the targeted mRNA. mRNA levels of the target gene can be quantitated by real time PCR (RT-PCR). Further, the protein levels can be determined in a variety of ways well known in the art, such as Western blot analysis with specific antibodies to the different targets allow direct monitoring of the reduction of targeted protein.

siRNA are introduced into cells by means of any transfection technique well known in the art. A single transfection of siRNA duplex can be performed, for instance, by using a cationic lipid, such as Lipofectamine 2000 Reagent (Invitrogen), followed by an assay of silencing efficiency 24, 48 and 72 hours after transfection.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. Good transfection is a non-trivial issue and needs to be carefully examined for each new cell line to be used. Transfection efficiency may be tested transfecting reporter genes, for example a CMV-driven EGFP-expression plasmid (e.g. from Clontech) or a B-Gal expression plasmid, and then assessed by phase contrast and/or fluorescence microscopy the next day.

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting.

Pharmaceutical Formulations and Routes of Administration.

The present invention may comprise the administration of one or more species of siNA molecule simultaneously. These species may be selected to target one or more target genes.

In one embodiment, a single type of siNA is administered in the therapeutic methods of the invention. In another embodiment, a siNA of the invention is administered in combination with another siNA of the invention and/or with one or more other non-siNA therapeutic agents useful in the treatment, prevention or management of a disease condition of the CNS. The term "in combination with" is not limited to the administration of therapeutic agents at exactly the same time, but rather it is meant that the siNAs of the invention and the other agent are administered to a patient in a sequence and within a time interval such that the benefit of the combination is greater than the benefit if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

The siNAs of the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). Formulations comprising one or more siNAs for use in the methods of the invention may be in numerous forms, and may depend on the various factors specific for each patient (e.g., the type and severity of disorder, type of siNA administered, age, body weight, response, and the past medical history of the patient), the number and type of siNAs in the formulation, the form of the composition (e.g., in liquid, semi-liquid or solid form) and/or the therapeutic regime (e.g. whether the therapeutic agent is administered over time as a slow infusion, a single bolus, once daily, several times a day or once every few days).

The siNA molecules of the invention and formulations or compositions thereof may be administered directly or topically as is generally known in the art. For example, a siNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

A siNA molecule of the invention may be complexed with membrane disruptive agents and/or a cationic lipid or helper lipid molecule.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

The formulations of the invention can be administered in dosage unit formulations containing conventional non-toxic pharmaceutically acceptable carriers, adjuvants and/or vehicles. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain siNA molecules of the invention can be expressed within cells from eukaryotic promoters. Recombinant vectors capable of expressing the siNA molecules can be delivered and persist in target cells. Alternatively, vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intramuscular administration, by administration to target cells ex-planted from a subject followed by reintroduction into the subject, or by any other means that would allow for introduction into the desired target cell.

Intranasal Administration of siNA.

Intranasal siNA delivery studies were carried out in GFP C57BL/6-TG (ACTB-EGFP) mice. This transgenic mouse line was bought from "The Jackson Laboratory". Transgenic mice have been used because homozygous mice for this transgene die within the first two weeks following birth. The transgenic mouse line with an "enhanced" GFP (EGFP) cDNA under the control of a chicken beta-actin promoter and cytomegalovirus enhancer makes all of the tissues, with the exception of erythrocytes and hair, appear green under excitation light. This strain was generated in C57BL/6 mice. The strain cDNA encoding enhanced green fluorescent protein (EGFP) was adjoined to the chicken beta actin promoter and cytomegalovirus enhancer. A bovine globin polyadenylation signal was also included in the construct. The EcoRI sites included in the PCR primers were used to introduce the amplified EGFP cDNA into a pCAGGS expression vector containing the chicken beta-actin promoter and cytomegalovirus enhancer, beta-actin intron and bovine globin polyadenylation signal. The entire insert with the promoter and coding sequence was excised with Bam-HI and SalI and gel-purified.

The siRNA used to downregulate EGFP mRNA expression targeted the following sequence in EGFP mRNA (SEQ ID NO: 321); 5'-GGC UAC GUC CAG GAG CGC ACC-3'. The sense strand of the siRNA duplex was 5'-P GGC UAC GUC CAG CGC ACC-3' (SEQ ID NO: 328) and the antisense strand was 5'-P GCG CUC CUG GAC GUA GCC UU-3' (SEQ ID NO: 322). siRNA duplex used in the experiments described below had two 2 thymidine nucleotide 3' overhang.

Experimental Protocol

For the intranasal delivery experiments C57BL/6-TG (ACTB-EGFP) male mice (8 week old) were used. Mice intranasally instilled with siRNA diluted in NaCl 0.9% were compared with control mice instilled with the vehicle (NaCl 0.9%). Animals were anesthetized with isofluorane and 20 µl of each solution were dropped into each nostril.

Different doses of siRNA vs EGFP mRNA (−/+ transfection lipid) were administered intranasally in a final volume of 20 µL. Control animals were treated with the vehicle alone. In all cases animals were sacrificed over a range of days after the administration of the drug in order to find the optimal time for interference.

For tissue analysis mice were sacrificed with $CO_2$ and brains were quickly dissected out onto an ice-cold plate. One half was processed for Western-blotting, while the other half was processed for immunohistochemistry.

The sample tissues were collected from different cerebral areas and analyzed by Western blot and real-time PCR. GFP expression in the different treatment conditions was measured with the assistance of an Adobe Photoshop program. Inhibition levels were obtained after normalization with respect to the beta-actin gene, which is constitutively expressed in the different tissues.

Experimental conditions were distributed as described in Table 1 (conditions were analyzed in duplicate or triplicate). Mice treated intranasally with one dose of 530 ug (40 nanomols) of the naked siRNA for GFP were named as mice 1, 2 and 3 and sacrificed at 3 and 5 days after inoculation of siRNA. Another experimental group (numbered as 4, 5, 6, 7, 8 and 9) consisted of animals treated with two doses of 265 ug (20 nanomols) of stabilized siRNA and sacrificed at 3, 5 and 8 days (Table 1).

The sample tissues were collected by two methods: one in protein buffer lysis medium and the other in RNAlater (Ambion). Afterwards small pieces of tissue were included in OCT in order to analyze the immunofluorescence signal of GFP protein in the tissue. All samples were stored at −80° C. until data processing.

TABLE 1

Schematic distribution of experimental conditions for intranasal siRNA delivery. Doses of siRNA are indicated in the table.

| Mouse number | Intranasal Therapeutic Treatment |
|---|---|
| CI, CII, CIII | Vehicle control dose |
| 1, 2, 3 | Single dose of 530 ug of siRNA |
| 4, 5 | Single dose of 265 ug of siRNA sacrificed at 3 days |
| 6, 7 | Single dose of 265 ug of siRNA sacrificed at 5 days |
| 8, 9 | Single dose of 265 ug of siRNA sacrificed at 8 days |

Extracts for Western blot analysis were prepared by homogenizing the brain areas in ice-cold extraction buffer consisting of 20 mM HEPES, pH 7.4, 100 mM NaCl, 20 mM NaF, 1% Triton X-100, 1 mM sodium orthovanadate, 5 mM EDTA, 1 µM okadaic acid and protease inhibitors (2 mM PMSF, 10 µg/ml aprotinin, 10 µg/ml leupeptin, and 10 µg/ml pepstatin). The samples were homogenized and centrifuged at 15,000×g for 20 min at 4° C. Protein contained in the supernatant was determined by Bradford. Thirty micrograms of total protein were separated by 10% sodium dodecyl sulphate-polyacrylamide gel electrophoresis and transferred to nitrocellulose membranes. The primary antibody used to detect transgene was EGFP antibody (1/1000) (Sigma) and anti-β-actin (1/2500) (Sigma). The membranes were incubated with the antibodies at 4° C. overnight in 5% nonfat dried milk. A secondary goat anti-mouse antibody (1/1000; Invitrogen, San Diego, Calif.) and ECL detection reagents (Amersham Biosciences, Arlington Heights, Ill.) were used for immunodetection. Protein levels were quantified by densitometry and GFP values were normalized with respect to actin to correct for any deviation in loaded amounts of protein.

Brains for immunohistochemistry were fixed in 4% paraformaldehyde in Sorensen's buffer overnight and cryoprotected in 30% sucrose solution. Brains were cut in thirty-micrometer sagittal sections on a freezing microtome (Leica, Nussloch, Germany) and collected in a cryoprotecting solution consisting of 30% ethylene glycol, 26% glycerol and phosphate buffer, pH 7.2. Next, brain sections were analyzed by fluorescence microscopy.

Tissues isolated in RNAlater were stored at −80° C. RNAlater was removed before RNA extraction because of its density. RNA is isolated with the Trizol Reagent (Invitrogen) according to the manufacturer protocol. DNAse treatment is done before measurement of GFP expression by quantitative PCR.

The siRNA application is made in order to determine whether siRNA delivery to the brain takes place. Since the goal is to determine the downregulation of GFP gene transcript, levels of fluorescence were measured following siRNA application. No secondary effects were observed in the animals along the experimental protocols.

Results

Central Nervous System In Vivo Delivery Model

Example 1

The siRNA application was made in order to determine the proper intranasal siRNA delivery in the Central Nervous System (CNS). Mice treated with 20 µl of NaCl (0.9%) (control), or with 20 µl siRNA at a concentration of 1 nmol/µl (Mouse 1), 2 nmol/µl (Mouse 2), or 2 nmol/µl+Transfection Lipid TransIT-TKO (Mouse 3), were sacrificed 48 h after treatment. No secondary effects were observed in the animals during the experimental protocols.

Samples of different regions of the CNS (cortex, hippocampus, striatum or bulb), as well as of different tissues (trachea, lung, nasal epithelium, esophagus) were extracted, and further analysed by Western blot with antibodies that specifically recognize GFP and immunoflurescence as described above. As a loading control, antibodies vs beta-actin were used.

Results of the GFP-expression inhibition levels in different regions of the CNS, after normalization with respect to beta-actin, are displayed in FIG. 1. As can be observed, the highest inhibitory effect was obtained with the dose of 2 nmol/µl, without transfection lipid. Further, inhibition was seen in various tissues of the CNS, including the cortex, hippocampus, striatum, and bulb. This result was also confirmed by real-time PCR.

Example 2

Different concentrations and timing of intranasal siRNA administration were using in GFP mouse models. Mice treated with 20 µl of NaCl (0.9%) (control), or with 20 µl siRNA at a concentration of 40 nmol or 20 nmol, were sacrificed at 3, 5, and 8 days after treatment. No secondary effects were observed in the animals during the experimental protocols.

Samples of different regions of the CNS (cortex, hippocampus, striatum, cerebellum, brainstem or bulb) were extracted, and further analysed by means of Western blot and immunofluorescence with antibodies that specifically recognize GFP. As a loading control, antibodies vs beta-actin were used.

Figure 2:
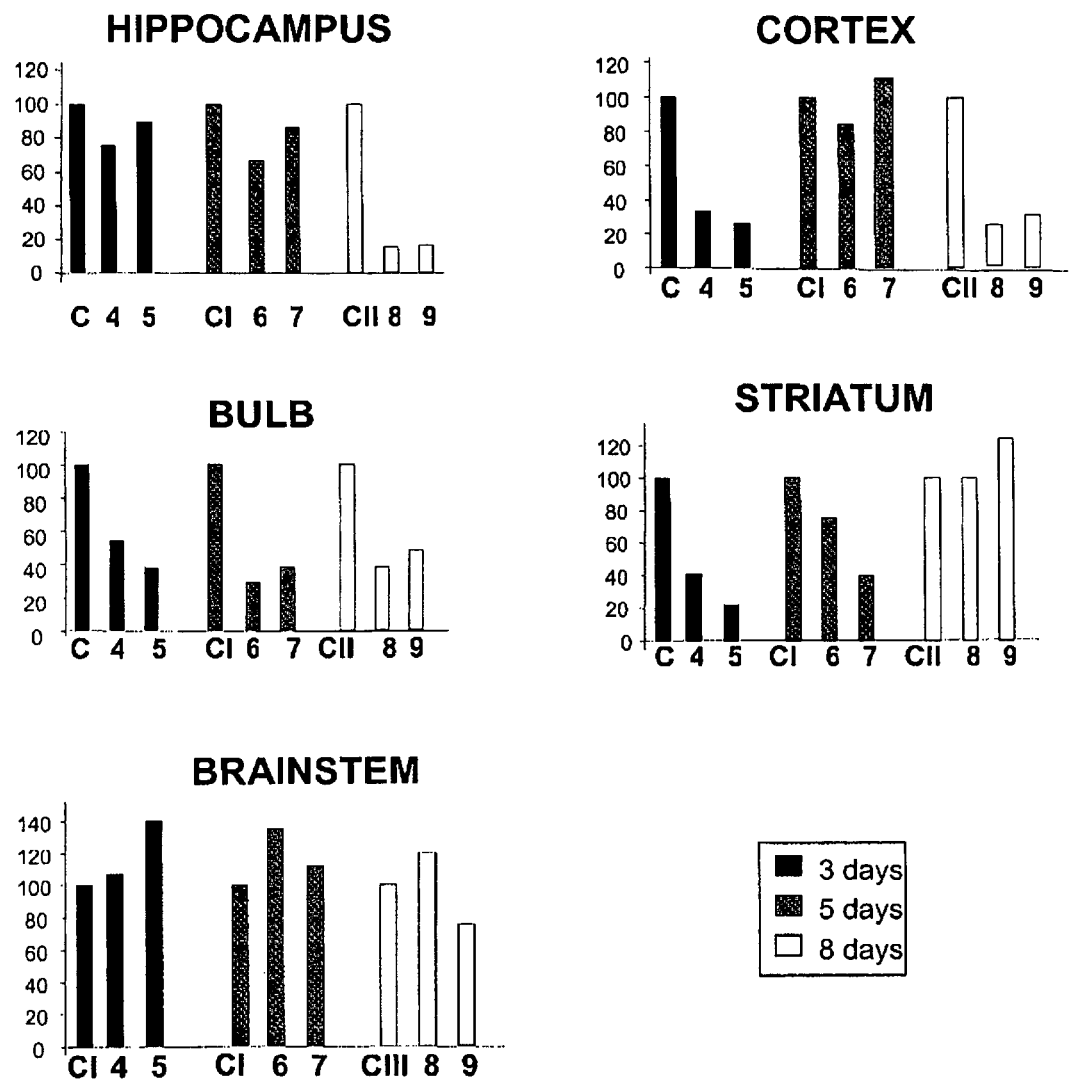
FIG. 2. siRNA reduces levels of GFP protein. siRNA designed against GFP was intranasally administered in transgenic GFP mice. Animals were sacrificed at different times and tissues collected were analyzed by Western Blot. Saline control was administered in mice CI, CII and CIII as control. The values show the GFP protein expression levels normalized to the GFP protein of control mice.
Figure 3:
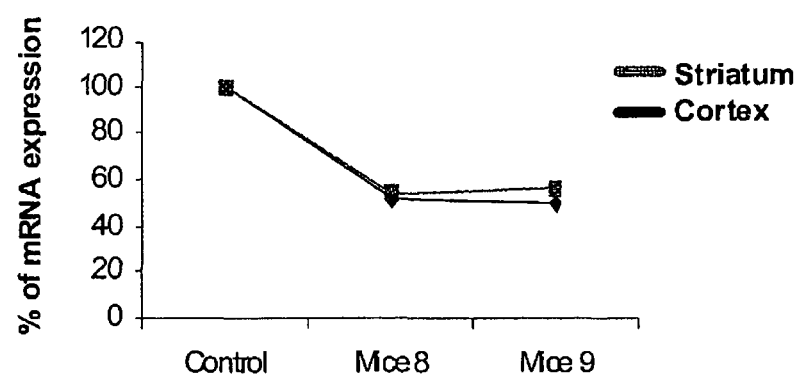
FIG. 3. siRNA reduces levels of GFP mRNA levels. siRNA designed against GFP was intranasally administered in transgenic GFP mice. Animals were sacrificed at different times and mRNA from different tissues collected. In this figure GFP mRNA expression of Striatum and Cortex was analyzed by quantitative PCR.

Results of the GFP-expression inhibition levels in different regions of the CNS, after normalization respect to beta-actin, are displayed in FIG. 2. As can be observed, the inhibitory effect was dependent on the cerebral area. Maximum GFP silencing was observed in cortex, hippocampus, striatum, and bulb. The results of the Western blot experiments were confirmed by quantitative PCR (FIG. 3). In FIG. 3 downregulation of GFP mRNA levels were analyzed in cortex and striatum and a clear reduction of these levels was observed in mouse conditions 8 and 9.

Example 3

Testing of MAPT siRNA Duplexes In Vitro

To check the specificity of the siRNAs, MAPT (microtubule associated protein tau) interference was analyzed in MAPT expressing cell cultures. The cells used for these experiments were human MDA-MB-435 cells. The levels of MAPT mRNA were analyzed after incubation with the corresponding siRNA duplexes. For linking siRNA knockdown to specific phenotypes in cultured cells, it is necessary to demonstrate the decrease of the targeted protein or at least to demonstrate the reduction of the targeted mRNA.

Transfection of siRNA Duplexes in Cell Cultures

Several examples of techniques for siRNA transfection are well known in the art. The transfection of siRNA duplexes consist of a single transfection of siRNA duplex using a cationic lipid, such as Lipofectamine 2000 Reagent (Invitrogen) and making a read out for silencing 24, 48 and 72 hours after transfection.

A typical transfection protocol can be performed as follows: For one well of a 6-well plate, we transfect using 100 nM for human MDA-MB-435 cells as final concentration of siRNA. Following Lipofectamine 2000 Reagent protocol, the day before transfection, we seed 2-4×10$^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 12.5 ul of 20 uM siRNA duplex (corresponding to 100 nM final concentration) or 25 ul of 20 uM siRNA duplex (corresponding to 200 nM final concentration) in 250 ul of DMEM and mix. Also, 6 ul of Lipofectamine 2000 is diluted in 250 ul of DMEM and mixed. After 5 minutes incubation at room temperature, the diluted oligomer (siRNA duplex) and the diluted Lipofectamine are combined to allow complex formation during 20 minutes incubation at room temperature.

Afterwards, we add the complexes drop-wise onto the cells with 2 ml of fresh growth medium low in antibiotics and mix gently by rocking the plate back and forth, to ensure uniform distribution of the transfection complexes. We incubate the cells under their normal growth conditions and the day after, the complexes are removed and fresh and complete growth medium is added. To monitor gene silencing, cells are collected at 24, 48 and 72 h post-transfection.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. Good transfection is a non-trivial issue and needs to be carefully examined for each new cell line to be used. Transfection efficiency may be tested transfecting reporter genes, for example a CMV-driven EGFP-expression plasmid (e.g. from Clontech) or a B-Gal expression plasmid, and then assessed by phase contrast and/ or fluorescence microscopy the next day.

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting.

After transfections, total RNA fractions extracted from cells were pre-treated with DNase I and used for reverse transcription using a random primer. PCR-amplified with a specific primer pair covering at least one exon-exon junction in order to control for amplification of pre-mRNAs. RT/PCR of a non-targeted mRNA is also needed as control. Effective depletion of the mRNA yet undetectable reduction of target protein may indicate that a large reservoir of stable protein may exist in the cell. Alternatively, Real-time PCR amplification can be used to test in a more precise way the mRNA decrease or disappearance. Quantitative PCR monitors the fluorescence emitted during the reaction as an indicator of amplicon production during each PCR cycle. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template.

To verify the interference pattern of the differentially expressed MARI gene in the cell cultures, qRT-PCR was performed according to the manufacturer protocol (Applied Biosystems). Reaction conditions were established for the Applied Biosystems 7300 and one step RT-PCR reaction was realized. Reaction volume of 25 ul consists of 2.times. SyBr green, Multiscribe™ reverse transcriptase 6.25U, RNase inhibitor and 50 mM of forward and reverse primers mixed with 100 ng of the template RNA. Specific primers to MAPT were designed and 18S was analyzed as housekeeping gene. The forward primer had the sequence: AAGAGCCGCCTG-CAGACA (SEQ ID NO: 323) while the reverse primer had the sequence GAGCCGATCTTGGACTTGACA (SEQ ID NO: 324).

Reverse transcription was carried out with an initial step of 30' at 48° C. Thermal cycling parameters were, 95° C. for 10 min, 40 cycles of 95° C. for 15 sec and 60° C. for 1 min. Dissociation curves were also analyzed to checked the amplification specificity. Threshold cycle (Ct) values of each sample were compared to the control 24 h sample to determine the percentage of downregulation of each gene after siRNA transfection.

In order to assess the specificity of the amplified PCR product a melting curve analysis was performed. The resulting melting curves allow discrimination between primer-dimers and specific PCR product.

In Vitro Assays for MAPT siRNAs.

Figure 4:
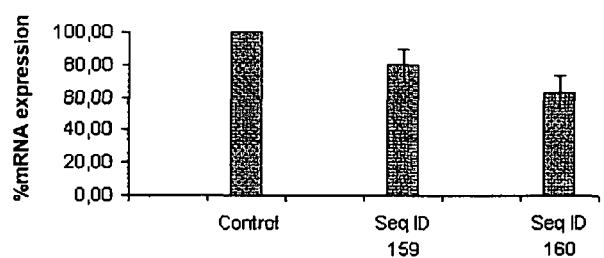
FIG. 4. siRNA reduces levels of MAPT gene transcript with different mutations. siRNAs designed to different mutations were analyzed Seq ID 159 (P301L mutation) and Seq ID 160 (R406W mutation). RNA was prepared from cells treated with the specific siRNAs for 48 h. The samples were analysed by quantitative PCR using specific primers for MAPT (described in the text). The values show the mean expression levels of different transcripts normalized to 18S relative to mock transfected cells as control.

To determine the inhibition of MAPT target using RNAi technology, the first step was to perform experiments in MDA-MB-435 cell cultures. These assays were performed in two parts. First, siRNAs designed against the MAPT mutations described in FIG. 7A and 7B were transfected. Afterwards, siRNAs against MAPT wild type were designed and the downregulation of MAPT after transfection was analysed. FIG. 4 shows representative results of quantitative PCR experiments for some of the mutations of MAPT previously described in FIGS. 7A and 7B. FIGS. 8A and 8B show the target sequences in MAPT (SEQ ID NO 1-160) against which siNA were designed. The siNA duplexes are given as SEQ ID NO 161-320 (FIGS. 8C-8F).

siRNAs designed against the mutations MAPT P301L (target region given as SEQ ID NO: 159) and MAPT R406W (target region given as SEQ ID NO: 160) to downregulate the levels of MAPT mRNA were analyzed. The values shown in FIG. 4 represent the mean of the percentage of si RNA interference over gene expression once normalized with the control cells and their standard deviations. Compared to the control cells, the level of the MAPT transcript at 48 h was reduced in a 20% after treatment with the siRNA targeting SEQ ID NO: 159 (specific to MAPT P301L). However, the reduction of MAPT upon transfection with the siRNA targeting SEQ ID NO: 160 (specific to MAPT R406W) reached up to 40% over the control levels.

Figure 5:
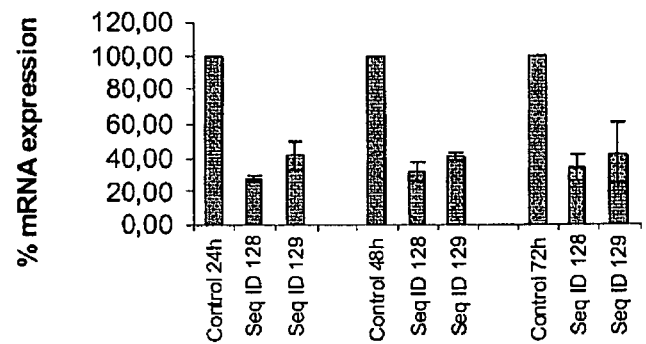
FIG. 5. siRNA reduces levels of MAPT gene transcript. RNA was prepared from MDA-MB-435 cells treated with different siRNAs for 24, 48 h and 72 h. The samples were analyzed by real time PCR using specific primers, described in the text. The values show the mean expression levels of different transcripts normalized to 18S relative to mock transfected control.

In a second round of experiments different siRNAs directed to MAPT wt were designed. Because MAPT has different isoforms, a sequence alignment was carried out and siRNAs were designed to the common region. The accession numbers of the Reference Sequences of the MAPT isoforms are listed as NM_005910, NM_016834 NM_016835 and NM_016841. Two different siRNAs to MAPT wt, corresponding to Seq ID 128 and Seq ID 139 were transfected in MDA-MB-435 cells. FIG. 5 below shows representative results of quantitative PCR analysis. The values represent the mean of the percentage of siRNA interference over each gene expression once normalized with the control cells and their standard deviations. Compared to the control cells, the level of MAPT transcript at 24, 48 or 72 h was significantly reduced after the specific siRNA treatment. siRNA corresponding to Seq ID 128, reduced the MAPT transcript in a 70% being this reduction very sustained along 48 h and 72 h. siRNA Seq ID 129 also reached a very good level of downregulation of MAPT about 60% compared to the mock transfected cells.

Example 4

Testing of MAPT siRNA Duplexes In Vivo

In order to provide a proof of concept of the intranasal delivery in a pathological model, MAPT involved in fronto-temporal dementia was downregulated in an appropriate MAPT Transgenic mouse model.

Mouse Strain Description

For generation of MAPT Transgenic Mice a plasmid pSGT42 (Montejo de Garcini et al., 1994) which encodes a human 4-repeat tau isoform with two N-terminal exons was used as a template to introduce the FTDP-17 mutations G272V and P301L separately with the Quikchange (Stratagene) procedure. A triple mutant tau cDNA was then assembled by ligation of the restriction fragments SacII/AseI (containing the G272V mutation) and AseI/HindIII (containing the P301L mutation) into the plasmid pSGTR406W (Perez, M., Lim, F., Arrasate, M., and Avila, J. (2000). The FTDP-17-linked mutation R406 W abolishes the interaction of phosphorylated tan with microtubules J. Neurochem. 74: 2583-2589) previously cut with SacII/HindIII to give rise to the plasmid pSGTVLW. The mutant tau open reading frame was excised from pSGTVLW as a BamIII/BglII fragment and ligated into the BamHI site of PBKCMV (Stratagene) in the forward orientation with respect to the CMV promoter to produce pBKVLW. The SalI/XhoI fragment of pRKVLW was then ligated into the XhoI site of pTSC21k (Luthi et al., 1997) in the forward orientation with respect to the thy1 promoter. The resulting plasmid pTTVLW was confirmed to encode the three specific amino acid changes G272V, P301L and R406W by sequencing of the SacII-HindIII region. Vector sequences were eliminated by NotI digestion and gel purification of the large fragment, which was then introduced by pronuclear injection into single-cell CBA 3C57BL/6 embryos. Founder mice were identified by PCR and crossed with wild-type C57BL/6 mice. All transgenic mice analyzed were heterozygotes. Mice were housed four per cage with food and water available ad libitum and maintained in a temperature-controlled environment on a 12/12 h light-dark cycle, with light onset at 07:00 h. PCR screening was performed on tail DNA using the oligonucleotides TT1, 5'-CTCTGCCCTCTGTTCTCTGG-3' (SEQ ID NO: 325, in exon 2 of the murine thy1 gene); TT2,5'-CCTGTC-CCCCAACCCGTACG-3' (SEQ ID NO: 326; at the 5' end of the human tau cDNA); and THY, 5'CGCTGATGGCTGGGT-TCATG-3' (SEQ ID NO: 327; in intron 2 of the murine thy1 gene). We used TT1 and TT2 to amplify a 470-bp product specifically from the transgene and not from endogenous murine DNA, while as an internal control for DNA, TT1 and THY were used to amplify a 450-bp product specifically from murine genomic DNA but not from the transgene. The transgenes were predominantly expressed in hippocampus and fronto temporal cortex.

Experimental Protocol

Different concentrations and timing of intranasal siRNA administration were using in transgenic MAPT mouse models. Mice were treated with 20 µl of NaCl (0.9%) (control), or with 20 µl siRNA at a concentration of 20 nmol.

Experimental conditions were distributed as described in Table 2 (conditions were analyzed in triplicate). Mice were treated intranasally with one or two doses of the siRNA for MAPT (Seq ID 160) and sacrificed at different times after inoculations of siRNA.

TABLE 2

Schematic distribution of experimental conditions for intranasal siRNA delivery. Doses of siRNA are indicated in the table.

| Mouse number | Intranasal Therapeutic Treatment |
|---|---|
| CI, CII, CIII | Vehicle control dose |
| 1, 2, 3 | Single dose of 265 ug of siRNA sacrificed at 3 days |
| 4, 5, 6 | Single dose of 265 ug of siRNA sacrificed at 5 days |
| 7, 8, 9 | Single dose of 265 ug of siRNA sacrificed at 7 days |
| 10, 11 | Two doses of 132 ug of siRNA sacrificed at 8 days |

Samples of different regions of the CNS (cortex, hippocampus, striatum, cerebellum, brainstem or bulb) were extracted, and further analysed by Western blot, immunofluorescence and quantitative PCR. Antibody that specifically recognize the mutated human MT were employed. As a loading control, antibodies vs beta-actin were used. MAPT expression in the different treatment conditions was measured with the assistance of an Adobe Photoshop program. Inhibition levels were obtained after normalization with respect to the beta-actin gene, which is constitutively expressed in the different tissues.

Figure 6:
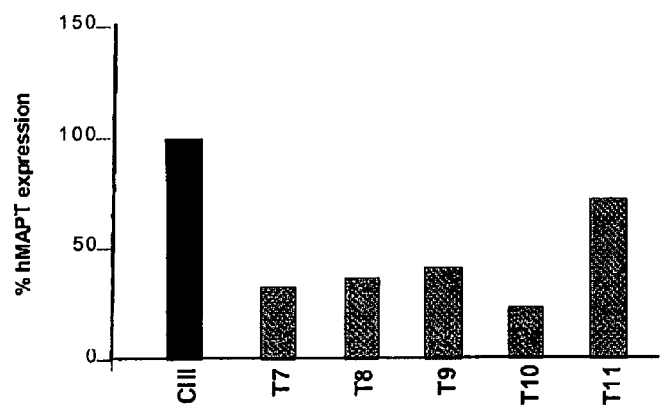
FIG. 6. siRNA Seq ID 160 designed to R406W mutation reduces MAPT protein levels in vivo. siRNA Seq ID 160 was intranasally administered in transgenic MAPT mice. Animals were sacrificed at seven days upon siRNA administration and hippocampus tissue was analyzed by Western Blot.

Results of the MAPT expression inhibition levels in different regions of the CNS, after normalization with respect to beta-actin, are displayed in FIG. 6. As can be observed, the inhibitory effect over MAPT expression was observed in hippocampus where the transgenic protein was expressed at high levels. The animals conditions in which the downregulation of the gene expression was highest corresponded to the animals sacrificed at 7 days after siRNA instillation. The results of the Western blot experiments were confirmed by quantitative PCR.

REFERENCES

Akashi H, Miyagishi M, Taira K. Suppression of gene expression by RNA interference in cultured plant cells. Antisense Nucleic Acid Drug Dev, 2001, 11(6):359-67.

Banerjee D, Slack F. Control of developmental timing by small temporal RNAs: a paradigm for RNA-mediated regulation of gene expression. Bioessays, 2002, 24(2):119-29.

Bosher J M, Labouesse M. RNA interference: genetic wand and genetic watchdog. Nat Cell Biol, 2000, 2(2):E31-6.

Caplen, N. J., Parrish, S., Imani, F., Fire, A. & Morgan, R. A. Specific inhibition of gene expression by small double stranded RNAs in invertebrate and vertebrate systems. Proc. Natl. Acad. Sci. USA, 2001, 98: 9742-9747.

Elbashir S M, Lendeckel W, Tuschl T. RNA interference is mediated by 21- and 22-nueleotide RNAs. Genes Dev, 2001, 15(2):188-200.

Fire A, Xu S, Montgomery M K, Kostas S A, Driver S E, Mello C C. Potent and specific genetic interference by double stranded RNA in *Caenorhabditis elegans*. Nature, 1998, 391(6669):806-11.

Gil J, Esteban M. Induction of apoptosis by the dsRNA-dependent protein kinase (PKR): mechanism of action. Apoptosis, 2000, 5(2):107-14.

Grosshans H, Slack F J. Micro-RNAs: small is plentiful. J Cell Biol, 2002, 156(1):17-21.

Hardy, J & Selkoe, D. J. The Amyloid Hypothesis of Alzheimer's Disease: Progress and Problems on the Road to Therapeutics. Science, 2002; Vol. 297. no. 5580, pp. 353-356.

Houlden, H., Baker, M., Morris, H. R., et al. Corticobasal degeneration and progressive supranuclear palsy share a common tau haplotype. Neurology, 2001; 56: 1702-1706.

Hutton, M., Lendon, C. L., Rizzu P., et al. Association of missense and 5'-splice-site mutations in tau with the inherited dementia FTDP-17. Nature, 1998; 393: 702-705.

Krutzfeldt J, Rajewsky N, Braich R, Rajeev K G, Tuschl T, Manoharan M, Stoffel M. Silencing of microRNAs in vivo with 'antagomirs'. Nature 2005, 438(7068):685-9.

Lee V M, Goedert M, Trojanowski J Q. Neurodegenerative tauopathies. Annu Rev Neurosci., 2001; 24:1121-59.

Lewis, J., Dickson, D. W., Lin, W., et al. Enhanced Neurofibrillary Degeneration in Transgenic Mice Expressing Mutant Tau and APP. Science, 2001; 293. no. 5534, pp. 1487-1491.

Miller V M, Gouvion C M, Davidson B L, Paulson H L. Targeting Alzheimer's disease genes with RNA interference: an efficient strategy for silencing mutant alleles. Nucleic Acids Res., 2004 Jan. 30; 32(2):661-8.

Miller V M, Xia H, Marrs G L, Gouvion C M, Lee G, Davidson B L, Paulson H L. Allele-specific silencing of dominant disease genes. Proc Natl Acad Sci USA, 2003 Jun. 10; 100(12):7195-200.

Mullan M, Crawford F, Axelman K, Houlden H, Lilius L, Winblad B, Lannfelt L. A pathogenic mutation for probable Alzheimer's disease in the APP gene at the N-terminus of beta-amyloid. Nat Genet., 1992 August; 1 (5):345-7.

Oddo S, Caccamo A, Shepherd J D, Murphy M P, Golde T E, Kayed R, Metherate R, Mattson M P, Alcbari Y, LaFerla F M. Triple-transgenic model of Alzheimer's disease with plaques and tangles: intracellular Abeta and synaptic dysfunction. Neuron, 2003; 39(3):409-21.

Paddison P J, Caudy A A, Bernstein E, Hannon G J, Conklin D S. Short hairpin RNAs (shRNAs) induce sequence-specific silencing in mammalian cells. Genes Dev, 2002, 16(8):948-58.

Poorkaj P, Bird T D, Wijsman E, Nemens E, Garruto R M, Anderson L, Andreadis A, Wiederholt W C, Raskind M, Schellenberg G D. Tau is a candidate gene for chromosome 17 frontotemporal dementia. Ann Neurol., 1998 June; 43(6):815-25.

Tuschl T, Zamore P D, Lehmann R, Bartel D P, Sharp P A. Targeted mRNA degradation by double-stranded RNA in vitro. Genes Dev., 1999; 13(24):3191-7.

Wianny F, Zernicka-Goetz M. Specific interference with gene function by double-stranded RNA in early mouse development. Nat Cell Biol., 2000, 2(2):70-5.

Williams B R. Role of the double-stranded RNA-activated protein kinase (PKR) in cell regulation. Biochem Soc Trans, 1997, 25(2):509-13.

The invention claimed is:

1. A method of treating a neurodegenerative disorder of the central nervous system (CNS) associated with abnormal tau expression or with a mutation in the tau gene in a patient in need thereof, said method comprising administering intranasally to said patient an effective amount of an siRNA which causes RNA interference in tau gene expression in the CNS, wherein the siRNA is targeted against a tau nucleic acid sequence as set forth in SEQ ID NO:160 and wherein the siRNA inhibits expression of the tau gene within CNS tissue.

2. The method of claim 1, wherein the neurodegenerative disorder of the CNS is dementia.

3. The method of claim 1, wherein the patient has altered levels of or a mutation in the tau target gene.

4. The method of claim 1, wherein the siRNA interferes with expression of a mutated allele of the tau target gene.

5. The method of claim 1, wherein the siRNA comprises a modified oligonucleotide.

6. The method of claim 1, wherein the siRNA is 40 base pairs or fewer in length.

7. The method of claim 1, wherein the siRNA has 3' overhangs.

8. The method of claim 7, wherein the 3' overhangs are dinucleotides.

9. The method of claim 8, wherein the dinucleotide overhangs comprise thymidine nucleotides.

10. The method of claim 1, wherein a plurality of different siRNAs is administered.

11. The method of claim 10, wherein said plurality of siRNAs is targeted to the same mRNA species.

12. The method of claim 10, wherein said plurality of siRNAs is targeted to different mRNA species.

13. The method of claim 1, wherein the siRNA is 40 base pairs or fewer in length and comprises the nucleotide sequence as set forth in SEQ ID NO:320.

14. A method of reducing expression of a tau target gene in the CNS of a non-human mammal, comprising intranasally administering an siRNA which targets the nucleic acid sequence as set forth in SEQ ID NO:160, and which causes RNA interference in the tau target gene within CNS tissue of the non-human mammal.

* * * * *

SEQUENCE LISTING

```
<160> NUMBER OF SEQ ID NOS: 328

<210> SEQ ID NO 1
<211> LENGTH: 19
<212> TYPE: DNA
<213> ORGANISM: Homo sapiens
<220> FEATURE:
<223> OTHER INFORMATION: MAPT

<400> SEQUENCE: 1
gtgatggaag atcacgctg                                                  19

<210> SEQ ID NO 2
<211> LENGTH: 19
<212> TYPE: DNA
<213> ORGANISM: Homo sapiens
<220> FEATURE:
<223> OTHER INFORMATION: MAPT

<400> SEQUENCE: 2
gatcacgctg ggacgtacg                                                  19

<210> SEQ ID NO 3
<211> LENGTH: 19
<212> TYPE: DNA
<213> ORGANISM: Homo sapiens
<220> FEATURE:
<223> OTHER INFORMATION: MAPT

<400> SEQUENCE: 3
agatcagggg ggctacacc                                                  19

<210> SEQ ID NO 4
<211> LENGTH: 19
<212> TYPE: DNA
<213> ORGANISM: Homo sapiens
<220> FEATURE:
<223> OTHER INFORMATION: MAPT

<400> SEQUENCE: 4
gatcaggggg gctacacca                                                  19

<210> SEQ ID NO 5
<211> LENGTH: 19
<212> TYPE: DNA
<213> ORGANISM: Homo sapiens
<220> FEATURE:
```

<223> OTHER INFORMATION: MAPT

<400> SEQUENCE: 5
gaccaagagg gtgacacgg                                          19

<210> SEQ ID NO 6
<211> LENGTH: 19
<212> TYPE: DNA
<213> ORGANISM: Homo sapiens
<220> FEATURE:
<223> OTHER INFORMATION: MAPT

<400> SEQUENCE: 6
gagggtgaca cggacgctg                                          19

<210> SEQ ID NO 7
<211> LENGTH: 19
<212> TYPE: DNA
<213> ORGANISM: Homo sapiens
<220> FEATURE:
<223> OTHER INFORMATION: MAPT

<400> SEQUENCE: 7
agaatctccc ctgcagacc                                          19

<210> SEQ ID NO 8
<211> LENGTH: 19
<212> TYPE: DNA
<213> ORGANISM: Homo sapiens
<220> FEATURE:
<223> OTHER INFORMATION: MAPT

<400> SEQUENCE: 8
gaatctcccc tgcagaccc                                          19

<210> SEQ ID NO 9
<211> LENGTH: 19
<212> TYPE: DNA
<213> ORGANISM: Homo sapiens
<220> FEATURE:
<223> OTHER INFORMATION: MAPT

<400> SEQUENCE: 9
tctcccctgc agacccca                                           19

<210> SEQ ID NO 10
<211> LENGTH: 19
<212> TYPE: DNA
<213> ORGANISM: Homo sapiens
<220> FEATURE:
<223> OTHER INFORMATION: MAPT

<400> SEQUENCE: 10
ccgggctctg aaacctctg                                          19

<210> SEQ ID NO 11
<211> LENGTH: 19
<212> TYPE: DNA
<213> ORGANISM: Homo sapiens
<220> FEATURE:
<223> OTHER INFORMATION: MAPT

<400> SEQUENCE: 11
acctctgatg ctaagagca                                          19

```
<210> SEQ ID NO 12
<211> LENGTH: 19
<212> TYPE: DNA
<213> ORGANISM: Homo sapiens
<220> FEATURE:
<223> OTHER INFORMATION: MAPT

<400> SEQUENCE: 12
cctctgatgc taagagcac                                              19

<210> SEQ ID NO 13
<211> LENGTH: 19
<212> TYPE: DNA
<213> ORGANISM: Homo sapiens
<220> FEATURE:
<223> OTHER INFORMATION: MAPT

<400> SEQUENCE: 13
gagcactcca acagcggaa                                              19

<210> SEQ ID NO 14
<211> LENGTH: 19
<212> TYPE: DNA
<213> ORGANISM: Homo sapiens
<220> FEATURE:
<223> OTHER INFORMATION: MAPT

<400> SEQUENCE: 14
cagcggaaga tgtgacagc                                              19

<210> SEQ ID NO 15
<211> LENGTH: 19
<212> TYPE: DNA
<213> ORGANISM: Homo sapiens
<220> FEATURE:
<223> OTHER INFORMATION: MAPT

<400> SEQUENCE: 15
gatgtgacag caccttag                                               19

<210> SEQ ID NO 16
<211> LENGTH: 19
<212> TYPE: DNA
<213> ORGANISM: Homo sapiens
<220> FEATURE:
<223> OTHER INFORMATION: MAPT

<400> SEQUENCE: 16
gcaggctgcc gcgcagccc                                              19

<210> SEQ ID NO 17
<211> LENGTH: 19
<212> TYPE: DNA
<213> ORGANISM: Homo sapiens
<220> FEATURE:
<223> OTHER INFORMATION: MAPT

<400> SEQUENCE: 17
ggaaccacag ctgaagaag                                              19

<210> SEQ ID NO 18
<211> LENGTH: 19
<212> TYPE: DNA
<213> ORGANISM: Homo sapiens
<220> FEATURE:
<223> OTHER INFORMATION: MAPT
```

```
<400> SEQUENCE: 18
ccacagctga agaagcagg                                                    19

<210> SEQ ID NO 19
<211> LENGTH: 19
<212> TYPE: DNA
<213> ORGANISM: Homo sapiens
<220> FEATURE:
<223> OTHER INFORMATION: MAPT

<400> SEQUENCE: 19
gaagcaggca ttggagaca                                                    19

<210> SEQ ID NO 20
<211> LENGTH: 19
<212> TYPE: DNA
<213> ORGANISM: Homo sapiens
<220> FEATURE:
<223> OTHER INFORMATION: MAPT

<400> SEQUENCE: 20
gcaggcattg gagacaccc                                                    19

<210> SEQ ID NO 21
<211> LENGTH: 19
<212> TYPE: DNA
<213> ORGANISM: Homo sapiens
<220> FEATURE:
<223> OTHER INFORMATION: MAPT

<400> SEQUENCE: 21
gacgaagctg ctggtcacg                                                    19

<210> SEQ ID NO 22
<211> LENGTH: 19
<212> TYPE: DNA
<213> ORGANISM: Homo sapiens

<400> SEQUENCE: 22
gctgctggtc acgtgaccc                                                    19

<210> SEQ ID NO 23
<211> LENGTH: 19
<212> TYPE: DNA
<213> ORGANISM: Homo sapiens
<220> FEATURE:
<223> OTHER INFORMATION: MAPT

<400> SEQUENCE: 23
gagcctgaaa gtggtaagg                                                    19

<210> SEQ ID NO 24
<211> LENGTH: 19
<212> TYPE: DNA
<213> ORGANISM: Homo sapiens
<220> FEATURE:
<223> OTHER INFORMATION: MAPT

<400> SEQUENCE: 24
agtggtaagg tggtccagg                                                    19

<210> SEQ ID NO 25
<211> LENGTH: 19
<212> TYPE: DNA
<213> ORGANISM: Homo sapiens
```

```
<220> FEATURE:
<223> OTHER INFORMATION: MAPT

<400> SEQUENCE: 25
gtggtaaggt ggtccagga                                                 19

<210> SEQ ID NO 26
<211> LENGTH: 19
<212> TYPE: DNA
<213> ORGANISM: Homo sapiens
<220> FEATURE:
<223> OTHER INFORMATION: MAPT

<400> SEQUENCE: 26
ggtggtccag gaaggcttc                                                 19

<210> SEQ ID NO 27
<211> LENGTH: 19
<212> TYPE: DNA
<213> ORGANISM: Homo sapiens
<220> FEATURE:
<223> OTHER INFORMATION: MAPT

<400> SEQUENCE: 27
ggcttcctcc gagagccag                                                 19

<210> SEQ ID NO 28
<211> LENGTH: 19
<212> TYPE: DNA
<213> ORGANISM: Homo sapiens
<220> FEATURE:
<223> OTHER INFORMATION: MAPT

<400> SEQUENCE: 28
ccttcgggga caggacctg                                                 19

<210> SEQ ID NO 29
<211> LENGTH: 19
<212> TYPE: DNA
<213> ORGANISM: Homo sapiens
<220> FEATURE:
<223> OTHER INFORMATION: MAPT

<400> SEQUENCE: 29
gcaccagctt ctaggagac                                                 19

<210> SEQ ID NO 30
<211> LENGTH: 19
<212> TYPE: DNA
<213> ORGANISM: Homo sapiens
<220> FEATURE:
<223> OTHER INFORMATION: MAPT

<400> SEQUENCE: 30
gggggcaggg ggcaaagag                                                 19

<210> SEQ ID NO 31
<211> LENGTH: 19
<212> TYPE: DNA
<213> ORGANISM: Homo sapiens
<220> FEATURE:
<223> OTHER INFORMATION: MAPT

<400> SEQUENCE: 31
agagaggccg gggagcaag                                                 19
```

<210> SEQ ID NO 32
<211> LENGTH: 19
<212> TYPE: DNA
<213> ORGANISM: Homo sapiens
<220> FEATURE:
<223> OTHER INFORMATION: MAPT

<400> SEQUENCE: 32
gagaggccgg ggagcaagg                                               19

<210> SEQ ID NO 33
<211> LENGTH: 19
<212> TYPE: DNA
<213> ORGANISM: Homo sapiens
<220> FEATURE:
<223> OTHER INFORMATION: MAPT

<400> SEQUENCE: 33
ggaggaggtg gatgaagac                                               19

<210> SEQ ID NO 34
<211> LENGTH: 19
<212> TYPE: DNA
<213> ORGANISM: Homo sapiens
<220> FEATURE:
<223> OTHER INFORMATION: MAPT

<400> SEQUENCE: 34
gaccgcgacg tcgatgagt                                               19

<210> SEQ ID NO 35
<211> LENGTH: 19
<212> TYPE: DNA
<213> ORGANISM: Homo sapiens
<220> FEATURE:
<223> OTHER INFORMATION: MAPT

<400> SEQUENCE: 35
gactcccctc cctccaagg                                               19

<210> SEQ ID NO 36
<211> LENGTH: 19
<212> TYPE: DNA
<213> ORGANISM: Homo sapiens
<220> FEATURE:
<223> OTHER INFORMATION: MAPT

<400> SEQUENCE: 36
ggcctcccca gcccaagat                                               19

<210> SEQ ID NO 37
<211> LENGTH: 19
<212> TYPE: DNA
<213> ORGANISM: Homo sapiens
<220> FEATURE:
<223> OTHER INFORMATION: MAPT

<400> SEQUENCE: 37
gatgggcggc ctccccaga                                               19

<210> SEQ ID NO 38
<211> LENGTH: 19
<212> TYPE: DNA
<213> ORGANISM: Homo sapiens
<220> FEATURE:
<223> OTHER INFORMATION: MAPT -continued

<400> SEQUENCE: 38
gccaccagca tcccaggct                                                19

<210> SEQ ID NO 39
<211> LENGTH: 19
<212> TYPE: DNA
<213> ORGANISM: Homo sapiens
<220> FEATURE:
<223> OTHER INFORMATION: MAPT

<400> SEQUENCE: 39
agtttccaca gagatccca                                                19

<210> SEQ ID NO 40
<211> LENGTH: 19
<212> TYPE: DNA
<213> ORGANISM: Homo sapiens
<220> FEATURE:
<223> OTHER INFORMATION: MAPT

<400> SEQUENCE: 40
gtttccacag agatcccag                                                19

<210> SEQ ID NO 41
<211> LENGTH: 19
<212> TYPE: DNA
<213> ORGANISM: Homo sapiens
<220> FEATURE:
<223> OTHER INFORMATION: MAPT

<400> SEQUENCE: 41
agggcaggat gccccctg                                                 19

<210> SEQ ID NO 42
<211> LENGTH: 19
<212> TYPE: DNA
<213> ORGANISM: Homo sapiens
<220> FEATURE:
<223> OTHER INFORMATION: MAPT

<400> SEQUENCE: 42
gggcaggatg ccccctgg                                                 19

<210> SEQ ID NO 43
<211> LENGTH: 19
<212> TYPE: DNA
<213> ORGANISM: Homo sapiens
<220> FEATURE:
<223> OTHER INFORMATION: MAPT

<400> SEQUENCE: 43
atcacaccca acgtgcaga                                                19

<210> SEQ ID NO 44
<211> LENGTH: 19
<212> TYPE: DNA
<213> ORGANISM: Homo sapiens
<220> FEATURE:
<223> OTHER INFORMATION: MAPT

<400> SEQUENCE: 44
tcacacccaa cgtgcagaa                                                19

<210> SEQ ID NO 45

```
<211> LENGTH: 19
<212> TYPE: DNA
<213> ORGANISM: Homo sapiens
<220> FEATURE:
<223> OTHER INFORMATION: MAPT

<400> SEQUENCE: 45
cgtgcagaag gagcaggcg                                               19

<210> SEQ ID NO 46
<211> LENGTH: 19
<212> TYPE: DNA
<213> ORGANISM: Homo sapiens
<220> FEATURE:
<223> OTHER INFORMATION: MAPT

<400> SEQUENCE: 46
ggagcaggcg cactcggag                                               19

<210> SEQ ID NO 47
<211> LENGTH: 19
<212> TYPE: DNA
<213> ORGANISM: Homo sapiens
<220> FEATURE:
<223> OTHER INFORMATION: MAPT

<400> SEQUENCE: 47
gggctgcatt tccaggggc                                               19

<210> SEQ ID NO 48
<211> LENGTH: 19
<212> TYPE: DNA
<213> ORGANISM: Homo sapiens
<220> FEATURE:
<223> OTHER INFORMATION: MAPT

<400> SEQUENCE: 48
aagaggctga ccttccaga                                               19

<210> SEQ ID NO 49
<211> LENGTH: 19
<212> TYPE: DNA
<213> ORGANISM: Homo sapiens
<220> FEATURE:
<223> OTHER INFORMATION: MAPT

<400> SEQUENCE: 49
agaggctgac cttccagag                                               19

<210> SEQ ID NO 50
<211> LENGTH: 19
<212> TYPE: DNA
<213> ORGANISM: Homo sapiens
<220> FEATURE:
<223> OTHER INFORMATION: MAPT

<400> SEQUENCE: 50
gaggctgacc ttccagagc                                               19

<210> SEQ ID NO 51
<211> LENGTH: 19
<212> TYPE: DNA
<213> ORGANISM: Homo sapiens
<220> FEATURE:
<223> OTHER INFORMATION: MAPT

<400> SEQUENCE: 51
```
aagcagcctg ctgctgctc                                              19

<210> SEQ ID NO 52
<211> LENGTH: 19
<212> TYPE: DNA
<213> ORGANISM: Homo sapiens
<220> FEATURE:
<223> OTHER INFORMATION: MAPT

<400> SEQUENCE: 52
agcagcctgc tgctgctcc                                              19

<210> SEQ ID NO 53
<211> LENGTH: 19
<212> TYPE: DNA
<213> ORGANISM: Homo sapiens
<220> FEATURE:
<223> OTHER INFORMATION: MAPT

<400> SEQUENCE: 53
gcagcctgct gctgctccg                                              19

<210> SEQ ID NO 54
<211> LENGTH: 19
<212> TYPE: DNA
<213> ORGANISM: Homo sapiens
<220> FEATURE:
<223> OTHER INFORMATION: MAPT

<400> SEQUENCE: 54
gcccgtcagc cgggtccct                                              19

<210> SEQ ID NO 55
<211> LENGTH: 19
<212> TYPE: DNA
<213> ORGANISM: Homo sapiens
<220> FEATURE:
<223> OTHER INFORMATION: MAPT

<400> SEQUENCE: 55
ctcaaagctc gcatggtca                                              19

<210> SEQ ID NO 56
<211> LENGTH: 19
<212> TYPE: DNA
<213> ORGANISM: Homo sapiens
<220> FEATURE:
<223> OTHER INFORMATION: MAPT

<400> SEQUENCE: 56
agctcgcatg gtcagtaaa                                              19

<210> SEQ ID NO 57
<211> LENGTH: 19
<212> TYPE: DNA
<213> ORGANISM: Homo sapiens
<220> FEATURE:
<223> OTHER INFORMATION: MAPT

<400> SEQUENCE: 57
gctcgcatgg tcagtaaaa                                              19

<210> SEQ ID NO 58
<211> LENGTH: 19
<212> TYPE: DNA

```
<213> ORGANISM: Homo sapiens
<220> FEATURE:
<223> OTHER INFORMATION: MAPT

<400> SEQUENCE: 58
aagcaaagac gggactgga                                              19

<210> SEQ ID NO 59
<211> LENGTH: 19
<212> TYPE: DNA
<213> ORGANISM: Homo sapiens
<220> FEATURE:
<223> OTHER INFORMATION: MAPT

<400> SEQUENCE: 59
agcaaagacg ggactggaa                                              19

<210> SEQ ID NO 60
<211> LENGTH: 19
<212> TYPE: DNA
<213> ORGANISM: Homo sapiens
<220> FEATURE:
<223> OTHER INFORMATION: MAPT

<400> SEQUENCE: 60
gcaaagacgg gactggaag                                              19

<210> SEQ ID NO 61
<211> LENGTH: 19
<212> TYPE: DNA
<213> ORGANISM: Homo sapiens
<220> FEATURE:
<223> OTHER INFORMATION: MAPT

<400> SEQUENCE: 61
agacgggact ggaagcgat                                              19

<210> SEQ ID NO 62
<211> LENGTH: 19
<212> TYPE: DNA
<213> ORGANISM: Homo sapiens
<220> FEATURE:
<223> OTHER INFORMATION: MAPT

<400> SEQUENCE: 62
gacgggactg gaagcgatg                                              19

<210> SEQ ID NO 63
<211> LENGTH: 19
<212> TYPE: DNA
<213> ORGANISM: Homo sapiens
<220> FEATURE:
<223> OTHER INFORMATION: MAPT

<400> SEQUENCE: 63
gcgatgacaa aaagccaa                                               19

<210> SEQ ID NO 64
<211> LENGTH: 19
<212> TYPE: DNA
<213> ORGANISM: Homo sapiens
<220> FEATURE:
<223> OTHER INFORMATION: MAPT

<400> SEQUENCE: 64
aaaagccaag acatccaca                                              19
```

<210> SEQ ID NO 65
<211> LENGTH: 19
<212> TYPE: DNA
<213> ORGANISM: Homo sapiens
<220> FEATURE:
<223> OTHER INFORMATION: MAPT

<400> SEQUENCE: 65
aaagccaaga catccacac                                               19

<210> SEQ ID NO 66
<211> LENGTH: 19
<212> TYPE: DNA
<213> ORGANISM: Homo sapiens
<220> FEATURE:
<223> OTHER INFORMATION: MAPT

<400> SEQUENCE: 66
aagccaagac atccacacg                                               19

<210> SEQ ID NO 67
<211> LENGTH: 19
<212> TYPE: DNA
<213> ORGANISM: Homo sapiens
<220> FEATURE:
<223> OTHER INFORMATION: MAPT

<400> SEQUENCE: 67
agccaagaca tccacacgt                                               19

<210> SEQ ID NO 68
<211> LENGTH: 19
<212> TYPE: DNA
<213> ORGANISM: Homo sapiens
<220> FEATURE:
<223> OTHER INFORMATION: MAPT

<400> SEQUENCE: 68
gccaagacat ccacacgtt                                               19

<210> SEQ ID NO 69
<211> LENGTH: 19
<212> TYPE: DNA
<213> ORGANISM: Homo sapiens
<220> FEATURE:
<223> OTHER INFORMATION: MAPT

<400> SEQUENCE: 69
gacatccaca cgttcctct                                               19

<210> SEQ ID NO 70
<211> LENGTH: 19
<212> TYPE: DNA
<213> ORGANISM: Homo sapiens
<220> FEATURE:
<223> OTHER INFORMATION: MAPT

<400> SEQUENCE: 70
aaccttgaaa aataggcct                                               19

<210> SEQ ID NO 71
<211> LENGTH: 19
<212> TYPE: DNA
<213> ORGANISM: Homo sapiens
<220> FEATURE:

```
<223> OTHER INFORMATION: MAPT

<400> SEQUENCE: 71
accttgaaaa ataggcctt                                                   19

<210> SEQ ID NO 72
<211> LENGTH: 19
<212> TYPE: DNA
<213> ORGANISM: Homo sapiens
<220> FEATURE:
<223> OTHER INFORMATION: MAPT

<400> SEQUENCE: 72
ccttgaaaaa taggccttg                                                   19

<210> SEQ ID NO 73
<211> LENGTH: 19
<212> TYPE: DNA
<213> ORGANISM: Homo sapiens
<220> FEATURE:
<223> OTHER INFORMATION: MAPT

<400> SEQUENCE: 73
aaataggcct tgccttagc                                                   19

<210> SEQ ID NO 74
<211> LENGTH: 19
<212> TYPE: DNA
<213> ORGANISM: Homo sapiens
<220> FEATURE:
<223> OTHER INFORMATION: MAPT

<400> SEQUENCE: 74
aataggcctt gccttagcc                                                   19

<210> SEQ ID NO 75
<211> LENGTH: 19
<212> TYPE: DNA
<213> ORGANISM: Homo sapiens
<220> FEATURE:
<223> OTHER INFORMATION: MAPT

<400> SEQUENCE: 75
ataggccttg ccttagccc                                                   19

<210> SEQ ID NO 76
<211> LENGTH: 19
<212> TYPE: DNA
<213> ORGANISM: Homo sapiens
<220> FEATURE:
<223> OTHER INFORMATION: MAPT

<400> SEQUENCE: 76
taggccttgc cttagcccc                                                   19

<210> SEQ ID NO 77
<211> LENGTH: 19
<212> TYPE: DNA
<213> ORGANISM: Homo sapiens
<220> FEATURE:
<223> OTHER INFORMATION: MAPT

<400> SEQUENCE: 77
acaccccact cctggtagc                                                   19
```

```
<210> SEQ ID NO 78
<211> LENGTH: 19
<212> TYPE: DNA
<213> ORGANISM: Homo sapiens
<220> FEATURE:
<223> OTHER INFORMATION: MAPT

<400> SEQUENCE: 78
caccccactc ctggtagct                                                    19

<210> SEQ ID NO 79
<211> LENGTH: 19
<212> TYPE: DNA
<213> ORGANISM: Homo sapiens
<220> FEATURE:
<223> OTHER INFORMATION: MAPT

<400> SEQUENCE: 79
ccctccagcc ctgctgtgt                                                    19

<210> SEQ ID NO 80
<211> LENGTH: 19
<212> TYPE: DNA
<213> ORGANISM: Homo sapiens
<220> FEATURE:
<223> OTHER INFORMATION: MAPT

<400> SEQUENCE: 80
acacgtctct tctgtcact                                                    19

<210> SEQ ID NO 81
<211> LENGTH: 19
<212> TYPE: DNA
<213> ORGANISM: Homo sapiens
<220> FEATURE:
<223> OTHER INFORMATION: MAPT

<400> SEQUENCE: 81
cacgtctctt ctgtcactt                                                    19

<210> SEQ ID NO 82
<211> LENGTH: 19
<212> TYPE: DNA
<213> ORGANISM: Homo sapiens
<220> FEATURE:
<223> OTHER INFORMATION: MAPT

<400> SEQUENCE: 82
ctggcagttc tggagcaaa                                                    19

<210> SEQ ID NO 83
<211> LENGTH: 19
<212> TYPE: DNA
<213> ORGANISM: Homo sapiens
<220> FEATURE:
<223> OTHER INFORMATION: MAPT

<400> SEQUENCE: 83
aggagatgaa actcaaggg                                                    19

<210> SEQ ID NO 84
<211> LENGTH: 19
<212> TYPE: DNA
<213> ORGANISM: Homo sapiens
<220> FEATURE:
<223> OTHER INFORMATION: MAPT
```

```
<400> SEQUENCE: 84
ggagatgaaa ctcaagggg                                                    19

<210> SEQ ID NO 85
<211> LENGTH: 19
<212> TYPE: DNA
<213> ORGANISM: Homo sapiens
<220> FEATURE:
<223> OTHER INFORMATION: MAPT

<400> SEQUENCE: 85
actcaagggg gctgatggt                                                    19

<210> SEQ ID NO 86
<211> LENGTH: 19
<212> TYPE: DNA
<213> ORGANISM: Homo sapiens
<220> FEATURE:
<223> OTHER INFORMATION: MAPT

<400> SEQUENCE: 86
ctcaaggggg ctgatggta                                                    19

<210> SEQ ID NO 87
<211> LENGTH: 19
<212> TYPE: DNA
<213> ORGANISM: Homo sapiens
<220> FEATURE:
<223> OTHER INFORMATION: MAPT

<400> SEQUENCE: 87
gggggctgat ggtaaaacg                                                    19

<210> SEQ ID NO 88
<211> LENGTH: 19
<212> TYPE: DNA
<213> ORGANISM: Homo sapiens
<220> FEATURE:
<223> OTHER INFORMATION: MAPT

<400> SEQUENCE: 88
aacgaagatc gccacaccg                                                    19

<210> SEQ ID NO 89
<211> LENGTH: 19
<212> TYPE: DNA
<213> ORGANISM: Homo sapiens
<220> FEATURE:
<223> OTHER INFORMATION: MAPT

<400> SEQUENCE: 89
acgaagatcg ccacaccgc                                                    19

<210> SEQ ID NO 90
<211> LENGTH: 19
<212> TYPE: DNA
<213> ORGANISM: Homo sapiens
<220> FEATURE:
<223> OTHER INFORMATION: MAPT

<400> SEQUENCE: 90
cgaagatcgc cacaccgcg                                                    19

<210> SEQ ID NO 91
<211> LENGTH: 19
```

```
<212> TYPE: DNA
<213> ORGANISM: Homo sapiens
<220> FEATURE:
<223> OTHER INFORMATION: MAPT

<400> SEQUENCE: 91
gatcgccaca ccgcgggga                                               19

<210> SEQ ID NO 92
<211> LENGTH: 19
<212> TYPE: DNA
<213> ORGANISM: Homo sapiens
<220> FEATURE:
<223> OTHER INFORMATION: MAPT

<400> SEQUENCE: 92
gggccaggcc aacgccacc                                               19

<210> SEQ ID NO 93
<211> LENGTH: 19
<212> TYPE: DNA
<213> ORGANISM: Homo sapiens
<220> FEATURE:
<223> OTHER INFORMATION: MAPT

<400> SEQUENCE: 93
cgccaccagg attccagca                                               19

<210> SEQ ID NO 94
<211> LENGTH: 19
<212> TYPE: DNA
<213> ORGANISM: Homo sapiens
<220> FEATURE:
<223> OTHER INFORMATION: MAPT

<400> SEQUENCE: 94
aaaccccgcc cgctccaaa                                               19

<210> SEQ ID NO 95
<211> LENGTH: 19
<212> TYPE: DNA
<213> ORGANISM: Homo sapiens

<400> SEQUENCE: 95
aaccccgccc gctccaaag                                               19

<210> SEQ ID NO 96
<211> LENGTH: 19
<212> TYPE: DNA
<213> ORGANISM: Homo sapiens
<220> FEATURE:
<223> OTHER INFORMATION: MAPT

<400> SEQUENCE: 96
accccgcccg ctccaaaga                                               19

<210> SEQ ID NO 97
<211> LENGTH: 19
<212> TYPE: DNA
<213> ORGANISM: Homo sapiens
<220> FEATURE:
<223> OTHER INFORMATION: MAPT

<400> SEQUENCE: 97
ccccgcccgc tccaaagac                                               19
```

```
<210> SEQ ID NO 98
<211> LENGTH: 19
<212> TYPE: DNA
<213> ORGANISM: Homo sapiens
<220> FEATURE:
<223> OTHER INFORMATION: MAPT

<400> SEQUENCE: 98
agacaccacc cagctctgg                                                   19

<210> SEQ ID NO 99
<211> LENGTH: 19
<212> TYPE: DNA
<213> ORGANISM: Homo sapiens
<220> FEATURE:
<223> OTHER INFORMATION: MAPT

<400> SEQUENCE: 99
gacaccaccc agctctggt                                                   19

<210> SEQ ID NO 100
<211> LENGTH: 19
<212> TYPE: DNA
<213> ORGANISM: Homo sapiens
<220> FEATURE:
<223> OTHER INFORMATION: MAPT

<400> SEQUENCE: 100
cctccaaaat cagggatc                                                    19

<210> SEQ ID NO 101
<211> LENGTH: 19
<212> TYPE: DNA
<213> ORGANISM: Homo sapiens
<220> FEATURE:
<223> OTHER INFORMATION: MAPT

<400> SEQUENCE: 101
aatcagggga tcgcagcgg                                                   19

<210> SEQ ID NO 102
<211> LENGTH: 19
<212> TYPE: DNA
<213> ORGANISM: Homo sapiens
<220> FEATURE:
<223> OTHER INFORMATION: MAPT

<400> SEQUENCE: 102
atcaggggat cgcagcggc                                                   19

<210> SEQ ID NO 103
<211> LENGTH: 19
<212> TYPE: DNA
<213> ORGANISM: Homo sapiens
<220> FEATURE:
<223> OTHER INFORMATION: MAPT

<400> SEQUENCE: 103 tcagggatc gcagcggct                                                    19

<210> SEQ ID NO 104
<211> LENGTH: 19
<212> TYPE: DNA
<213> ORGANISM: Homo sapiens
<220> FEATURE:
<223> OTHER INFORMATION: MAPT
```

```
<400> SEQUENCE: 104
ccccacccac ccgggagcc                                                    19

<210> SEQ ID NO 105
<211> LENGTH: 19
<212> TYPE: DNA
<213> ORGANISM: Homo sapiens
<220> FEATURE:
<223> OTHER INFORMATION: MAPT

<400> SEQUENCE: 105
gaaggtggca gtggtccgt                                                    19

<210> SEQ ID NO 106
<211> LENGTH: 19
<212> TYPE: DNA
<213> ORGANISM: Homo sapiens
<220> FEATURE:
<223> OTHER INFORMATION: MAPT

<400> SEQUENCE: 106
ggtggcagtg gtccgtact                                                    19

<210> SEQ ID NO 107
<211> LENGTH: 19
<212> TYPE: DNA
<213> ORGANISM: Homo sapiens
<220> FEATURE:
<223> OTHER INFORMATION: MAPT

<400> SEQUENCE: 107
gtcgccgtct tccgccaag                                                    19

<210> SEQ ID NO 108
<211> LENGTH: 19
<212> TYPE: DNA
<213> ORGANISM: Homo sapiens
<220> FEATURE:
<223> OTHER INFORMATION: MAPT

<400> SEQUENCE: 108
gagccgcctg cagacagcc                                                    19

<210> SEQ ID NO 109
<211> LENGTH: 19
<212> TYPE: DNA
<213> ORGANISM: Homo sapiens
<220> FEATURE:
<223> OTHER INFORMATION: MAPT

<400> SEQUENCE: 109
gaatgtcaag tccaagatc                                                    19

<210> SEQ ID NO 110
<211> LENGTH: 19
<212> TYPE: DNA
<213> ORGANISM: Homo sapiens
<220> FEATURE:
<223> OTHER INFORMATION: MAPT

<400> SEQUENCE: 110
tgtcaagtcc aagatcggc                                                    19

<210> SEQ ID NO 111
```

```
<211> LENGTH: 19
<212> TYPE: DNA
<213> ORGANISM: Homo sapiens
<220> FEATURE:
<223> OTHER INFORMATION: MAPT

<400> SEQUENCE: 111
gtccaagatc ggctccact                                                    19

<210> SEQ ID NO 112
<211> LENGTH: 19
<212> TYPE: DNA
<213> ORGANISM: Homo sapiens
<220> FEATURE:
<223> OTHER INFORMATION: MAPT

<400> SEQUENCE: 112
gatcggctcc actgagaac                                                    19

<210> SEQ ID NO 113
<211> LENGTH: 19
<212> TYPE: DNA
<213> ORGANISM: Homo sapiens
<220> FEATURE:
<223> OTHER INFORMATION: MAPT

<400> SEQUENCE: 113
cctgaagcac cagccggga                                                    19

<210> SEQ ID NO 114
<211> LENGTH: 19
<212> TYPE: DNA
<213> ORGANISM: Homo sapiens
<220> FEATURE:
<223> OTHER INFORMATION: MAPT

<400> SEQUENCE: 114
gcaccagccg ggaggcggg                                                    19

<210> SEQ ID NO 115
<211> LENGTH: 19
<212> TYPE: DNA
<213> ORGANISM: Homo sapiens
<220> FEATURE:
<223> OTHER INFORMATION: MAPT

<400> SEQUENCE: 115
ggtgcagata attaataag                                                    19

<210> SEQ ID NO 116
<211> LENGTH: 19
<212> TYPE: DNA
<213> ORGANISM: Homo sapiens
<220> FEATURE:
<223> OTHER INFORMATION: MAPT

<400> SEQUENCE: 116
ttaataagaa gctggatct                                                    19

<210> SEQ ID NO 117
<211> LENGTH: 19
<212> TYPE: DNA
<213> ORGANISM: Homo sapiens
<220> FEATURE:
<223> OTHER INFORMATION: MAPT

<400> SEQUENCE: 117
```
taagaagctg gatcttagc                                                19

<210> SEQ ID NO 118
<211> LENGTH: 19
<212> TYPE: DNA
<213> ORGANISM: Homo sapiens
<220> FEATURE:
<223> OTHER INFORMATION: MAPT

<400> SEQUENCE: 118
gaagctggat cttagcaac                                                19

<210> SEQ ID NO 119
<211> LENGTH: 19
<212> TYPE: DNA
<213> ORGANISM: Homo sapiens
<220> FEATURE:
<223> OTHER INFORMATION: MAPT

<400> SEQUENCE: 119
gctggatctt agcaacgtc                                                19

<210> SEQ ID NO 120
<211> LENGTH: 19
<212> TYPE: DNA
<213> ORGANISM: Homo sapiens
<220> FEATURE:
<223> OTHER INFORMATION: MAPT

<400> SEQUENCE: 120
cgtccagtcc aagtgtggc                                                19

<210> SEQ ID NO 121
<211> LENGTH: 19
<212> TYPE: DNA
<213> ORGANISM: Homo sapiens
<220> FEATURE:
<223> OTHER INFORMATION: MAPT

<400> SEQUENCE: 121
gtgtggctca aaggataat                                                19

<210> SEQ ID NO 122
<211> LENGTH: 19
<212> TYPE: DNA
<213> ORGANISM: Homo sapiens
<220> FEATURE:
<223> OTHER INFORMATION: MAPT

<400> SEQUENCE: 122
aggataatat caaacacgt                                                19

<210> SEQ ID NO 123
<211> LENGTH: 19
<212> TYPE: DNA
<213> ORGANISM: Homo sapiens
<220> FEATURE:
<223> OTHER INFORMATION: MAPT

<400> SEQUENCE: 123
ggataatatc aaacacgtc                                                19

<210> SEQ ID NO 124
<211> LENGTH: 19
<212> TYPE: DNA

```
<213> ORGANISM: Homo sapiens
<220> FEATURE:
<223> OTHER INFORMATION: MAPT

<400> SEQUENCE: 124
tatcaaacac gtcccggga                                                19

<210> SEQ ID NO 125
<211> LENGTH: 19
<212> TYPE: DNA
<213> ORGANISM: Homo sapiens
<220> FEATURE:
<223> OTHER INFORMATION: MAPT

<400> SEQUENCE: 125
acacgtcccg ggaggcggc                                                19

<210> SEQ ID NO 126
<211> LENGTH: 19
<212> TYPE: DNA
<213> ORGANISM: Homo sapiens
<220> FEATURE:
<223> OTHER INFORMATION: MAPT

<400> SEQUENCE: 126
cacgtcccgg gaggcggca                                                19

<210> SEQ ID NO 127
<211> LENGTH: 19
<212> TYPE: DNA
<213> ORGANISM: Homo sapiens
<220> FEATURE:
<223> OTHER INFORMATION: MAPT

<400> SEQUENCE: 127
atagtctaca aaccagttg                                                19

<210> SEQ ID NO 128
<211> LENGTH: 19
<212> TYPE: DNA
<213> ORGANISM: Homo sapiens
<220> FEATURE:
<223> OTHER INFORMATION: MAPT

<400> SEQUENCE: 128
tagtctacaa accagttga                                                19

<210> SEQ ID NO 129
<211> LENGTH: 19
<212> TYPE: DNA
<213> ORGANISM: Homo sapiens
<220> FEATURE:
<223> OTHER INFORMATION: MAPT

<400> SEQUENCE: 129
accagttgac ctgagcaag                                                19

<210> SEQ ID NO 130
<211> LENGTH: 19
<212> TYPE: DNA
<213> ORGANISM: Homo sapiens
<220> FEATURE:
<223> OTHER INFORMATION: MAPT

<400> SEQUENCE: 130
ccagttgacc tgagcaagg                                                19
```

<210> SEQ ID NO 131
<211> LENGTH: 19
<212> TYPE: DNA
<213> ORGANISM: Homo sapiens
<220> FEATURE:
<223> OTHER INFORMATION: MAPT

<400> SEQUENCE: 131
ggtgacctcc aagtgtggc                                               19

<210> SEQ ID NO 132
<211> LENGTH: 19
<212> TYPE: DNA
<213> ORGANISM: Homo sapiens
<220> FEATURE:
<223> OTHER INFORMATION: MAPT

<400> SEQUENCE: 132
gtgtggctca ttaggcaac                                               19

<210> SEQ ID NO 133
<211> LENGTH: 19
<212> TYPE: DNA
<213> ORGANISM: Homo sapiens
<220> FEATURE:
<223> OTHER INFORMATION: MAPT

<400> SEQUENCE: 133
catccatcat aaaccagga                                               19

<210> SEQ ID NO 134
<211> LENGTH: 19
<212> TYPE: DNA
<213> ORGANISM: Homo sapiens
<220> FEATURE:
<223> OTHER INFORMATION: MAPT

<400> SEQUENCE: 134
accaggaggt ggccaggtg                                               19

<210> SEQ ID NO 135
<211> LENGTH: 19
<212> TYPE: DNA
<213> ORGANISM: Homo sapiens
<220> FEATURE:
<223> OTHER INFORMATION: MAPT

<400> SEQUENCE: 135
ccaggaggtg gccaggtgg                                               19

<210> SEQ ID NO 136
<211> LENGTH: 19
<212> TYPE: DNA
<213> ORGANISM: Homo sapiens
<220> FEATURE:
<223> OTHER INFORMATION: MAPT

<400> SEQUENCE: 136
gtaaaatctg agaagcttg                                               19

<210> SEQ ID NO 137
<211> LENGTH: 19
<212> TYPE: DNA
<213> ORGANISM: Homo sapiens
<220> FEATURE:

<223> OTHER INFORMATION: MPAT

<400> SEQUENCE: 137
aatctgagaa gcttgactt                    19

<210> SEQ ID NO 138
<211> LENGTH: 19
<212> TYPE: DNA
<213> ORGANISM: Homo sapiens
<220> FEATURE:
<223> OTHER INFORMATION: MAPT

<400> SEQUENCE: 138
atctgagaag cttgacttc                    19

<210> SEQ ID NO 139
<211> LENGTH: 19
<212> TYPE: DNA
<213> ORGANISM: Homo sapiens
<220> FEATURE:
<223> OTHER INFORMATION: MAPT

<400> SEQUENCE: 139
tctgagaagc ttgacttca                    19

<210> SEQ ID NO 140
<211> LENGTH: 19
<212> TYPE: DNA
<213> ORGANISM: Homo sapiens
<220> FEATURE:
<223> OTHER INFORMATION: MAPT

<400> SEQUENCE: 140
gcttgacttc aaggacaga                    19

<210> SEQ ID NO 141
<211> LENGTH: 19
<212> TYPE: DNA
<213> ORGANISM: Homo sapiens
<220> FEATURE:
<223> OTHER INFORMATION: MAPT

<400> SEQUENCE: 141
ggacagagtc cagtcgaag                    19

<210> SEQ ID NO 142
<211> LENGTH: 19
<212> TYPE: DNA
<213> ORGANISM: Homo sapiens
<220> FEATURE:
<223> OTHER INFORMATION: MAPT

<400> SEQUENCE: 142
gattgggtcc ctggacaat                    19

<210> SEQ ID NO 143
<211> LENGTH: 19
<212> TYPE: DNA
<213> ORGANISM: Homo sapiens
<220> FEATURE:
<223> OTHER INFORMATION: MAPT

<400> SEQUENCE: 143
tatcacccac gtccctggc                    19

```
<210> SEQ ID NO 144
<211> LENGTH: 19
<212> TYPE: DNA
<213> ORGANISM: Homo sapiens
<220> FEATURE:
<223> OTHER INFORMATION: MAPT

<400> SEQUENCE: 144
ataaaaagat tgaaaccca                                               19

<210> SEQ ID NO 145
<211> LENGTH: 19
<212> TYPE: DNA
<213> ORGANISM: Homo sapiens
<220> FEATURE:
<223> OTHER INFORMATION: MAPT

<400> SEQUENCE: 145
taaaaagatt gaaacccac                                               19

<210> SEQ ID NO 146
<211> LENGTH: 19
<212> TYPE: DNA
<213> ORGANISM: Homo sapiens
<220> FEATURE:
<223> OTHER INFORMATION: MAPT

<400> SEQUENCE: 146
aaagattgaa acccacaag                                               19

<210> SEQ ID NO 147
<211> LENGTH: 19
<212> TYPE: DNA
<213> ORGANISM: Homo sapiens
<220> FEATURE:
<223> OTHER INFORMATION: MAPT

<400> SEQUENCE: 147
aagattgaaa cccacaagc                                               19

<210> SEQ ID NO 148
<211> LENGTH: 19
<212> TYPE: DNA
<213> ORGANISM: Homo sapiens
<220> FEATURE:
<223> OTHER INFORMATION: MAPT

<400> SEQUENCE: 148
agattgaaac ccacaagct                                               19

<210> SEQ ID NO 149
<211> LENGTH: 19
<212> TYPE: DNA
<213> ORGANISM: Homo sapiens
<220> FEATURE:
<223> OTHER INFORMATION: MAPT

<400> SEQUENCE: 149
gattgaaacc cacaagctg                                               19

<210> SEQ ID NO 150
<211> LENGTH: 19
<212> TYPE: DNA
<213> ORGANISM: Homo sapiens
<220> FEATURE:
<223> OTHER INFORMATION: MAPT
```

```
<400> SEQUENCE: 150
acccacaagc tgaccttcc                                                    19

<210> SEQ ID NO 151
<211> LENGTH: 19
<212> TYPE: DNA
<213> ORGANISM: Homo sapiens
<220> FEATURE:
<223> OTHER INFORMATION: MAPT

<400> SEQUENCE: 151
cccacaagct gaccttccg                                                    19

<210> SEQ ID NO 152
<211> LENGTH: 19
<212> TYPE: DNA
<213> ORGANISM: Homo sapiens
<220> FEATURE:
<223> OTHER INFORMATION: MAPT

<400> SEQUENCE: 152
gctgaccttc cgcgagaac                                                    19

<210> SEQ ID NO 153
<211> LENGTH: 19
<212> TYPE: DNA
<213> ORGANISM: Homo sapiens
<220> FEATURE:
<223> OTHER INFORMATION: MAPT

<400> SEQUENCE: 153
cgccaaagcc aagacagac                                                    19

<210> SEQ ID NO 154
<211> LENGTH: 19
<212> TYPE: DNA
<213> ORGANISM: Homo sapiens
<220> FEATURE:
<223> OTHER INFORMATION: MAPT

<400> SEQUENCE: 154
agccaagaca gaccacggg                                                    19

<210> SEQ ID NO 155
<211> LENGTH: 19
<212> TYPE: DNA
<213> ORGANISM: Homo sapiens
<220> FEATURE:
<223> OTHER INFORMATION: MAPT

<400> SEQUENCE: 155
gccaagacag accacgggg                                                    19

<210> SEQ ID NO 156
<211> LENGTH: 19
<212> TYPE: DNA
<213> ORGANISM: Homo sapiens
<220> FEATURE:
<223> OTHER INFORMATION: MAPT

<400> SEQUENCE: 156
gacagaccac ggggcggag                                                    19

<210> SEQ ID NO 157
<211> LENGTH: 19
```

```
<212> TYPE: DNA
<213> ORGANISM: Homo sapiens
<220> FEATURE:
<223> OTHER INFORMATION: MAPT

<400> SEQUENCE: 157
gtcgccagtg gtgtctggg                                              19

<210> SEQ ID NO 158
<211> LENGTH: 19
<212> TYPE: DNA
<213> ORGANISM: Homo sapiens
<220> FEATURE:
<223> OTHER INFORMATION: MAPT

<400> SEQUENCE: 158
tgtctcctcc accggcagc                                              19

<210> SEQ ID NO 159
<211> LENGTH: 19
<212> TYPE: DNA
<213> ORGANISM: Homo sapiens
<220> FEATURE:
<223> OTHER INFORMATION: MAPT

<400> SEQUENCE: 159
tattaaacac gtcctggga                                              19

<210> SEQ ID NO 160
<211> LENGTH: 19
<212> TYPE: DNA
<213> ORGANISM: Homo sapiens
<220> FEATURE:
<223> OTHER INFORMATION: MAPT

<400> SEQUENCE: 160
acgtctccat ggcatctca                                              19

<210> SEQ ID NO 161
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 161
gugauggaag aucacgcug                                              19

<210> SEQ ID NO 162
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 162
gaucacgcug ggacguacg                                              19

<210> SEQ ID NO 163
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 163
```
gaucacgcug ggacguacg        19

<210> SEQ ID NO 164
<211> LENGTH: 20
<212> TYPE: RNA
<213> ORGANISM: Homo sapiens
<220> FEATURE:
<223> OTHER INFORMATION: RNAi, 5'-3' strand of double stranded molecule

<400> SEQUENCE: 164 cuagucccc cgauguggua        20

<210> SEQ ID NO 165
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 165
gaccaagagg gugacacgg        19

<210> SEQ ID NO 166
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 166
gagggugaca cggacgcug        19

<210> SEQ ID NO 167
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 167
agaaucuccc cugcagacc        19

<210> SEQ ID NO 168
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 168
gaaucucccc ugcagaccc        19

<210> SEQ ID NO 169
<211> LENGTH: 19
<212> TYPE: RNA
<213> ORGANISM: Homo sapiens

<400> SEQUENCE: 169
ucuccccugc agaccccca        19

<210> SEQ ID NO 170
<211> LENGTH: 19
<212> TYPE: RNA
<213> ORGANISM: Homo sapiens
<220> FEATURE:
<223> OTHER INFORMATION: RNAi, 5'-3' strand of double stranded molecule

```
<400> SEQUENCE: 170
ccgggcucug aaaccucug                                               19

<210> SEQ ID NO 171
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 171
accucugaug cuaagagca                                               19

<210> SEQ ID NO 172
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 172
ccucugaugc uaagagcac                                               19

<210> SEQ ID NO 173
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 173
gagcacucca acagcggaa                                               19

<210> SEQ ID NO 174
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 174
cagcggaaga ugugacagc                                               19

<210> SEQ ID NO 175
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 175
gcaggcugcc gcgcagccc                                               19

<210> SEQ ID NO 176
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 176
ggaaccacag cugaagaag                                               19

<210> SEQ ID NO 177
```

```
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 177
ccacagcuga agaagcagg                                                    19

<210> SEQ ID NO 178
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 178
gaagcaggca uuggagaca                                                    19

<210> SEQ ID NO 179
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 179
gcaggcauug gagacaccc                                                    19

<210> SEQ ID NO 180
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 180
gacgaagcug cuggucacg                                                    19

<210> SEQ ID NO 181
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 181
gacgaagcug cuggucacg                                                    19

<210> SEQ ID NO 182
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 182
gcugcugguc acgugaccc                                                    19

<210> SEQ ID NO 183
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 183
```

```
gagccugaaa gugguaagg                                               19

<210> SEQ ID NO 184
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 184
agugguaagg ugguccagg                                               19

<210> SEQ ID NO 185
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 185
gugguaaggu gguccagga                                               19

<210> SEQ ID NO 186
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 186
ggugguccag gaaggcuuc                                               19

<210> SEQ ID NO 187
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 187
ggcuuccucc gagagccag                                               19

<210> SEQ ID NO 188
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 188
ccuucgggga caggaccug                                               19

<210> SEQ ID NO 189
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 189
gcaccagcuu cuaggagac                                               19

<210> SEQ ID NO 190
<211> LENGTH: 19
<212> TYPE: RNA
```

```
<213> ORGANISM: Homo sapiens
<220> FEATURE:
<223> OTHER INFORMATION: RNAi, 5'-3' strand of double stranded molecule

<400> SEQUENCE: 190
gggggcaggg ggcaaagag                                                19

<210> SEQ ID NO 191
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 191
agagaggccg gggagcaag                                                19

<210> SEQ ID NO 192
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 192
gagaggccgg ggagcaagg                                                19

<210> SEQ ID NO 193
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 193
ggaggaggug gaugaagac                                                19

<210> SEQ ID NO 194
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 194
gaccgcgacg ucgaugagu                                                19

<210> SEQ ID NO 195
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 195
gacuccccuc ccuccaagg                                                19

<210> SEQ ID NO 196
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 196
ggccucccca gcccaagau                                                19
```

<210> SEQ ID NO 197
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 197
gaugggcggc cuccccaga                                                   19

<210> SEQ ID NO 198
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 198
gccaccagca ucccaggcu                                                   19

<210> SEQ ID NO 199
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 199 aguuccaca gagauccca                                                    19

<210> SEQ ID NO 200
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 200
guuuccacag agaucccag                                                   19

<210> SEQ ID NO 201
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 201
agggcaggau gcccccug                                                    19

<210> SEQ ID NO 202
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 202
gggcaggaug cccccugg                                                    19

<210> SEQ ID NO 203
<211> LENGTH: 19
<212> TYPE: RNA
<213> ORGANISM: Homo sapiens
<220> FEATURE:

<223> OTHER INFORMATION: RNAi, 5'-3' strand of double stranded molecule

<400> SEQUENCE: 203
aucacaccca acgugcaga                                                    19

<210> SEQ ID NO 204
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 204
ucacacccaa cgugcagaa                                                    19

<210> SEQ ID NO 205
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 205
cgugcagaag gagcaggcg                                                    19

<210> SEQ ID NO 206
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 206
ggagcaggcg cacucggag                                                    19

<210> SEQ ID NO 207
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 207
gggcugcauu uccaggggc                                                    19

<210> SEQ ID NO 208
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 208
aagaggcuga ccuuccaga                                                    19

<210> SEQ ID NO 209
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 209
agaggcugac cuuccagag                                                    19

```
<210> SEQ ID NO 210
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 210
gaggcugacc uuccagagc                                                  19

<210> SEQ ID NO 211
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 211
aagcagccug cugcugcuc                                                  19

<210> SEQ ID NO 212
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 212
agcagccugc ugcugcucc                                                  19

<210> SEQ ID NO 213
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 213
gcagccugcu gcugcuccg                                                  19

<210> SEQ ID NO 214
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 214
gcccgucagc cgggucccu                                                  19

<210> SEQ ID NO 215
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 215
cucaaagcuc gcaugguca                                                  19

<210> SEQ ID NO 216
<211> LENGTH: 19
<212> TYPE: RNA
<213> ORGANISM: Homo sapiens
<220> FEATURE:
<223> OTHER INFORMATION: RNAi, 5'-3' strand of double stranded molecule
```

```
<400> SEQUENCE: 216
agcucgcaug gucaguaaa                                                    19

<210> SEQ ID NO 217
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 217
gcucgcaugg ucaguaaaa                                                    19

<210> SEQ ID NO 218
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 218
aagcaaagac gggacugga                                                    19

<210> SEQ ID NO 219
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 219
agcaaagacg ggacuggaa                                                    19

<210> SEQ ID NO 220
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 220
gcaaagacgg gacuggaag                                                    19

<210> SEQ ID NO 221
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 221
agacgggacu ggaagcgau                                                    19

<210> SEQ ID NO 222
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 222
gacgggacug gaagcgaug                                                    19

<210> SEQ ID NO 223
<211> LENGTH: 19
```

```
<212> TYPE: RNA
<213> ORGANISM: Homo sapiens
<220> FEATURE:
<223> OTHER INFORMATION: RNAi, 5'-3' strand of double stranded molecule

<400> SEQUENCE: 223
gcgaugacaa aaagccaa                                              19

<210> SEQ ID NO 224
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 224
aaaagccaag acauccaca                                             19

<210> SEQ ID NO 225
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 225
aaagccaaga cauccacac                                             19

<210> SEQ ID NO 226
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 226
aagccaagac auccacacg                                             19

<210> SEQ ID NO 227
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 227
agccaagaca uccacacgu                                             19

<210> SEQ ID NO 228
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 228
gccaagacau ccacacguu                                             19

<210> SEQ ID NO 229
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 229
```
gacauccaca cguccucu                                                      19

<210> SEQ ID NO 230
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 230 aaccugaaa aauaggccu                                                      19

<210> SEQ ID NO 231
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 231 accugaaaa auaggccuu                                                      19

<210> SEQ ID NO 232
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 232 ccugaaaaa uaggccuug                                                      19

<210> SEQ ID NO 233
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 233
aaauaggccu ugccuuagc                                                     19

<210> SEQ ID NO 234
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 234
aauaggccuu gccuuagcc                                                     19

<210> SEQ ID NO 235
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 235
auaggccuug ccuuagccc                                                     19

<210> SEQ ID NO 236
<211> LENGTH: 19
<212> TYPE: RNA
<213> ORGANISM: Homo sapiens

```
<220> FEATURE:
<223> OTHER INFORMATION: RNAi, 5'-3' strand of double stranded molecule

<400> SEQUENCE: 236
uaggccuugc cuuagcccc                                                  19

<210> SEQ ID NO 237
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 237
acaccccacu ccugguagc                                                  19

<210> SEQ ID NO 238
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 238
caccccacuc cugguagcu                                                  19

<210> SEQ ID NO 239
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 239
cccuccagcc cugcugugu                                                  19

<210> SEQ ID NO 240
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 240
acacgucucu ucugucacu                                                  19

<210> SEQ ID NO 241
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 241
cacgucucuu cugucacuu                                                  19

<210> SEQ ID NO 242
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 242
cuggcaguuc uggagcaaa                                                  19
```

```
<210> SEQ ID NO 243
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 243
aggagaugaa acucaaggg                                                19

<210> SEQ ID NO 244
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 244
ggagaugaaa cucaagggg                                                19

<210> SEQ ID NO 245
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 245
acucaagggg gcugauggu                                                19

<210> SEQ ID NO 246
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 246
cucaaggggg cugauggua                                                19

<210> SEQ ID NO 247
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 247
gggggcugau gguaaaacg                                                19

<210> SEQ ID NO 248
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 248
aacgaagauc gccacaccg                                                19

<210> SEQ ID NO 249
<211> LENGTH: 19
<212> TYPE: RNA
<213> ORGANISM: Homo sapiens
<220> FEATURE:
<223> OTHER INFORMATION: RNAi, 5'-3' strand of double stranded molecule
```

```
<400> SEQUENCE: 249
acgaagaucg ccacaccgc                                                19

<210> SEQ ID NO 250
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 250
cgaagaucgc cacaccgcg                                                19

<210> SEQ ID NO 251
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 251
gaucgccaca ccgcgggga                                                19

<210> SEQ ID NO 252
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 252
gggccaggcc aacgccacc                                                19

<210> SEQ ID NO 253
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 253
cgccaccagg auuccagca                                                19

<210> SEQ ID NO 254
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 254 aaacccgcc cgcuccaaa                                                 19

<210> SEQ ID NO 255
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 255
aaccccgccc gcuccaaag                                                19

<210> SEQ ID NO 256
```

```
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 256
accccgcccg cuccaaaga                                                   19

<210> SEQ ID NO 257
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 257
ccccgcccgc uccaaagac                                                   19

<210> SEQ ID NO 258
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 258
agacaccacc cagcucugg                                                   19

<210> SEQ ID NO 259
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 259
gacaccaccc agcucuggu                                                   19

<210> SEQ ID NO 260
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 260
ccuccaaaau cagggqauc                                                   19

<210> SEQ ID NO 261
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 261
aaucagggga ucgcagcgg                                                   19

<210> SEQ ID NO 262
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 262
```
aucaggggau cgcagcggc                                                19

<210> SEQ ID NO 263
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 263
ucaggggauc gcagcggcu                                                19

<210> SEQ ID NO 264
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 264
ccccacccac ccgggagcc                                                19

<210> SEQ ID NO 265
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 265
gaagguggca gugguccgu                                                19

<210> SEQ ID NO 266
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 266
gguggcagug guccguacu                                                19

<210> SEQ ID NO 267
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 267
gucgccgucu uccgccaag                                                19

<210> SEQ ID NO 268
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 268
gagccgccug cagacagcc                                                19

<210> SEQ ID NO 269
<211> LENGTH: 19
<212> TYPE: RNA

```
<213> ORGANISM: Homo sapiens
<220> FEATURE:
<223> OTHER INFORMATION: RNAi, 5'-3' strand of double stranded molecule

<400> SEQUENCE: 269
gaaugucaag uccaagauc                                                   19

<210> SEQ ID NO 270
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 270
ugucaagucc aagaucggc                                                   19

<210> SEQ ID NO 271
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 271
guccaagauc ggcuccacu                                                   19

<210> SEQ ID NO 272
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 272
gaucggcucc acugagaac                                                   19

<210> SEQ ID NO 273
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 273
ccugaagcac cagccggga                                                   19

<210> SEQ ID NO 274
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 274
gcaccagccg ggaggcggg                                                   19

<210> SEQ ID NO 275
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 275
ggugcagaua auuaauaag                                                   19
```

```
<210> SEQ ID NO 276
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 276
uuaauaagaa gcuggaucu                                                19

<210> SEQ ID NO 277
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 277
uaagaagcug gaucuuagc                                                19

<210> SEQ ID NO 278
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 278
gaagcuggau cuuagcaac                                                19

<210> SEQ ID NO 279
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 279
gcuggaucuu agcaacguc                                                19

<210> SEQ ID NO 280
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 280
cguccagucc aaguguggc                                                19

<210> SEQ ID NO 281
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 281
guguggcuca aaggauaau                                                19

<210> SEQ ID NO 282
<211> LENGTH: 19
<212> TYPE: RNA
<213> ORGANISM: Homo sapiens
<220> FEATURE:
```

```
<223> OTHER INFORMATION: RNAi, 5'-3' strand of double stranded molecule

<400> SEQUENCE: 282
aggauaauau caaacacgu                                                    19

<210> SEQ ID NO 283
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 283
ggauaauauc aaacacguc                                                    19

<210> SEQ ID NO 284
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 284
uaucaaacac gucccggga                                                    19

<210> SEQ ID NO 285
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 285
acacgucccg ggaggcggc                                                    19

<210> SEQ ID NO 286
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 286
cacgucccgg gaggcggca                                                    19

<210> SEQ ID NO 287
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 287
auagucuaca aaccaguug                                                    19

<210> SEQ ID NO 288
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 288
uagucuacaa accaguuga                                                    19
```

```
<210> SEQ ID NO 289
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 289
accaguugac cugagcaag                                                  19

<210> SEQ ID NO 290
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 290
ccaguugacc ugagcaagg                                                  19

<210> SEQ ID NO 291
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 291
ggugaccucc aaguguggc                                                  19

<210> SEQ ID NO 292
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 292
guguggcuca uuaggcaac                                                  19

<210> SEQ ID NO 293
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 293
cauccaucau aaaccagga                                                  19

<210> SEQ ID NO 294
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 294
accaggaggu ggccaggug                                                  19

<210> SEQ ID NO 295
<211> LENGTH: 19
<212> TYPE: RNA
<213> ORGANISM: Homo sapiens
<220> FEATURE:
<223> OTHER INFORMATION: RNAi, 5'-3' strand of double stranded molecule
```

-continued

<400> SEQUENCE: 295
ccaggaggug gccaggugg                                                      19

<210> SEQ ID NO 296
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 296
guaaaaucug agaagcuug                                                      19

<210> SEQ ID NO 297
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 297
aaucugagaa gcuugacuu                                                      19

<210> SEQ ID NO 298
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 298
aucugagaag cuugacuuc                                                      19

<210> SEQ ID NO 299
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 299
ucugagaagc uugacuuca                                                      19

<210> SEQ ID NO 300
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 300
gcuugacuuc aaggacaga                                                      19

<210> SEQ ID NO 301
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 301
ggacagaguc cagucgaag                                                      19

<210> SEQ ID NO 302
<211> LENGTH: 19

```
<212> TYPE: RNA
<213> ORGANISM: Homo sapiens
<220> FEATURE:
<223> OTHER INFORMATION: RNAi, 5'-3' strand of double stranded molecule

<400> SEQUENCE: 302
gauugggucc cuggacaau                                                  19

<210> SEQ ID NO 303
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 303
uaucacccac gucccuggc                                                  19

<210> SEQ ID NO 304
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 304
auaaaaagau ugaaaccca                                                  19

<210> SEQ ID NO 305
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 305
uaaaaagauu gaaacccac                                                  19

<210> SEQ ID NO 306
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 306
aaagauugaa acccacaag                                                  19

<210> SEQ ID NO 307
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 307
aagauugaaa cccacaagc                                                  19

<210> SEQ ID NO 308
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 308
```
agauugaaac ccacaagcu                                                    19

<210> SEQ ID NO 309
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 309
gauugaaacc cacaagcug                                                    19

<210> SEQ ID NO 310
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 310
acccacaagc ugaccuucc                                                    19

<210> SEQ ID NO 311
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 311
cccacaagcu gaccuuccg                                                    19

<210> SEQ ID NO 312
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 312
gcugaccuuc cgcgagaac                                                    19

<210> SEQ ID NO 313
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 313
cgccaaagcc aagacagac                                                    19

<210> SEQ ID NO 314
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 314
agccaagaca gaccacggg                                                    19

<210> SEQ ID NO 315
<211> LENGTH: 19
<212> TYPE: RNA
<213> ORGANISM: Homo sapiens

```
<220> FEATURE:
<223> OTHER INFORMATION: RNAi, 5'-3' strand of double stranded molecule

<400> SEQUENCE: 315
gccaagacag accacgggg                                                    19

<210> SEQ ID NO 316
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 316
gacagaccac ggggcggag                                                    19

<210> SEQ ID NO 317
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 317
gucgccagug gugucuggg                                                    19

<210> SEQ ID NO 318
<211> LENGTH: 19
<212> TYPE: RNA
<213> ORGANISM: Homo sapiens
<220> FEATURE:
<223> OTHER INFORMATION: RNAi, 5'-3' strand of double stranded molecule

<400> SEQUENCE: 318
ugucuccucc accggcagc                                                    19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uauuaaacac guccuggga                                                    19

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
acgucuccau ggcaucuca                                                    19

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
```

-continued

```
ggcuacgucc aggagcgcac c                                              21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-P

<400> SEQUENCE: 322
ugcgcuccug gacguagccu u                                              21

<210> SEQ ID NO 323
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
aagagccgcc tgcagaca                                                  18

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gagccgatct tggacttgac a                                              21

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ctctgccctc tgttctctgg                                                20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
cctgtccccc aacccgtacg                                                20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 327
cgctgatggc tgggttcatg                                              20

<210> SEQ ID NO 328
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-P

<400> SEQUENCE: 328
ggcuacgucc agcgcacc                                                18
```